US010195261B2

(12) United States Patent
Miller et al.

(10) Patent No.: US 10,195,261 B2
(45) Date of Patent: *Feb. 5, 2019

(54) ADJUVANT COMPOSITIONS AND RELATED METHODS

(71) Applicant: VaxLiant, LLC, Lincoln, NE (US)

(72) Inventors: Timothy J Miller, Lincoln, NE (US); Mary Ann Pfannenstiel, Lincoln, NE (US)

(73) Assignee: VaxLiant, LLC, Lincoln, NE (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/953,230

(22) Filed: Nov. 27, 2015

(65) Prior Publication Data
US 2016/0144037 A1 May 26, 2016

Related U.S. Application Data

(60) Provisional application No. 62/084,698, filed on Nov. 26, 2014.

(51) Int. Cl.
A61K 39/395 (2006.01)
A61K 39/02 (2006.01)
A61K 39/00 (2006.01)
A61K 39/12 (2006.01)
A61K 39/39 (2006.01)

(52) U.S. Cl.
CPC .......... *A61K 39/02* (2013.01); *A61K 39/0005* (2013.01); *A61K 39/12* (2013.01); *A61K 39/39* (2013.01); *A61K 2039/52* (2013.01); *A61K 2039/525* (2013.01); *A61K 2039/53* (2013.01); *A61K 2039/55511* (2013.01); *A61K 2039/55555* (2013.01); *A61K 2039/55577* (2013.01)

(58) Field of Classification Search
None
See application file for complete search history.

(56) References Cited

U.S. PATENT DOCUMENTS

| 2,909,462 | A | 10/1959 | Warfield et al. | |
| 5,961,970 | A | 10/1999 | Lowell et al. | |
| 9,636,397 | B2 * | 5/2017 | Miller | A61K 39/39 |
| 2008/0292663 | A1 * | 11/2008 | Gerber | A61K 9/0019 424/280.1 |
| 2010/0021416 | A1 | 1/2010 | Lichter et al. | |
| 2011/0207952 | A1 | 8/2011 | Avila | |
| 2014/0056940 | A1 | 2/2014 | Dominowski et al. | |
| 2015/0044242 | A1 | 2/2015 | Gerber et al. | |
| 2017/0202959 | A1 * | 7/2017 | Miller | A61K 39/39 |

FOREIGN PATENT DOCUMENTS

| WO | 2009/156960 A2 | 12/2009 |
| WO | 2013/138334 A1 | 9/2013 |
| WO | 2014/071219 A1 | 5/2014 |
| WO | 2016/086222 A1 | 6/2016 |
| WO | 2016/154432 A1 | 9/2016 |

OTHER PUBLICATIONS

Aguilar et al., "Vaccine adjuvants revisited", Vaccine, 2007, pp. 3752-3762, vol. 25.
International Search Report and Written Opinion from related International Application No. PCT/US2015/62836, dated Feb. 5, 2016; 8 pgs.
International Search Report and Written Opinion from related International Application No. PCT/US2016/024003, dated Jun. 27, 2016; 11 pgs.
Office Action from related U.S. Appl. No. 15/079,936, dated Jul. 6, 2016; 15 pgs.
Office Action from related U.S. Appl. No. 15/079,936, dated Jan. 9, 2017; 7 pgs.
Office Action from related U.S. Appl. No. 15/467,585, dated Jan. 17, 2018; 28 pgs.
Hodgson et al., "Recent advances in non-viral vectors for gene therapy & vaccination", Cell & Gene Therapy Insights, 2017, pp. 95-101, vol. 3, No. 2.
Luke et al., "Improved antibiotic-free DNA vaccine vectors utilizing a novel RNA based plasmid selection system", Vaccine, 2009, pp. 6454-6459, vol. 27, No. 46.
Luke et al., "Coexpressed RIG-I Agonist Enhances Humoral Immune Response to Influenza Virus DNA Vaccine", Journal of Virology, 2011, pp. 1370-1383, vol. 85, No. 3.
Luke et al., "Improved antibiotic-free plasmid vector design by incorporation of transient expression enhancers", Gene Therapy, 2011, pp. 334-343, vol. 18.
Pereira et al., "DNA Vaccines Approach: From Concepts to Applications", World Journal of Vaccines, 2014, pp. 50-71, vol. 4.
Dey et al., "Use of a polyanionic carbomer, Carbopol971P, in combination with MF59, improves antibody responses to HIV-1 envelope glycoprotein", Vaccine, 2012, pp. 2749-2759, vol. 30, No. 17.
O'Hagan, "MF59 is a safe and potent vaccine adjuvant that enhances protection against influenza virus infection", Expert Review of Vaccines, Future Drugs, London, GB, 2007, pp. 699-710, vol. 6, No. 5.
Supplementary European Search Report from European Application No. 15862713.3, dated Jun. 22, 2018; 10 pgs.

* cited by examiner

Primary Examiner — Yunsoo Kim
(74) Attorney, Agent, or Firm — Polsinelli PC

(57) ABSTRACT

The present disclosure provides for an adjuvant composition that is suited for injectable as well as transdermal administration. The adjuvant composition generally comprises a lipophile, a polymer of acrylic or methacrylic acid, saline, cholesterol, a saponin, and sodium hydroxide. A vaccine composition is also provided for that generally includes the vaccine composition of the present disclosure and an antigen. A method for vaccinating animals and humans utilizing the adjuvant composition of the present disclosure is also provided.

17 Claims, 3 Drawing Sheets

Figure 1:
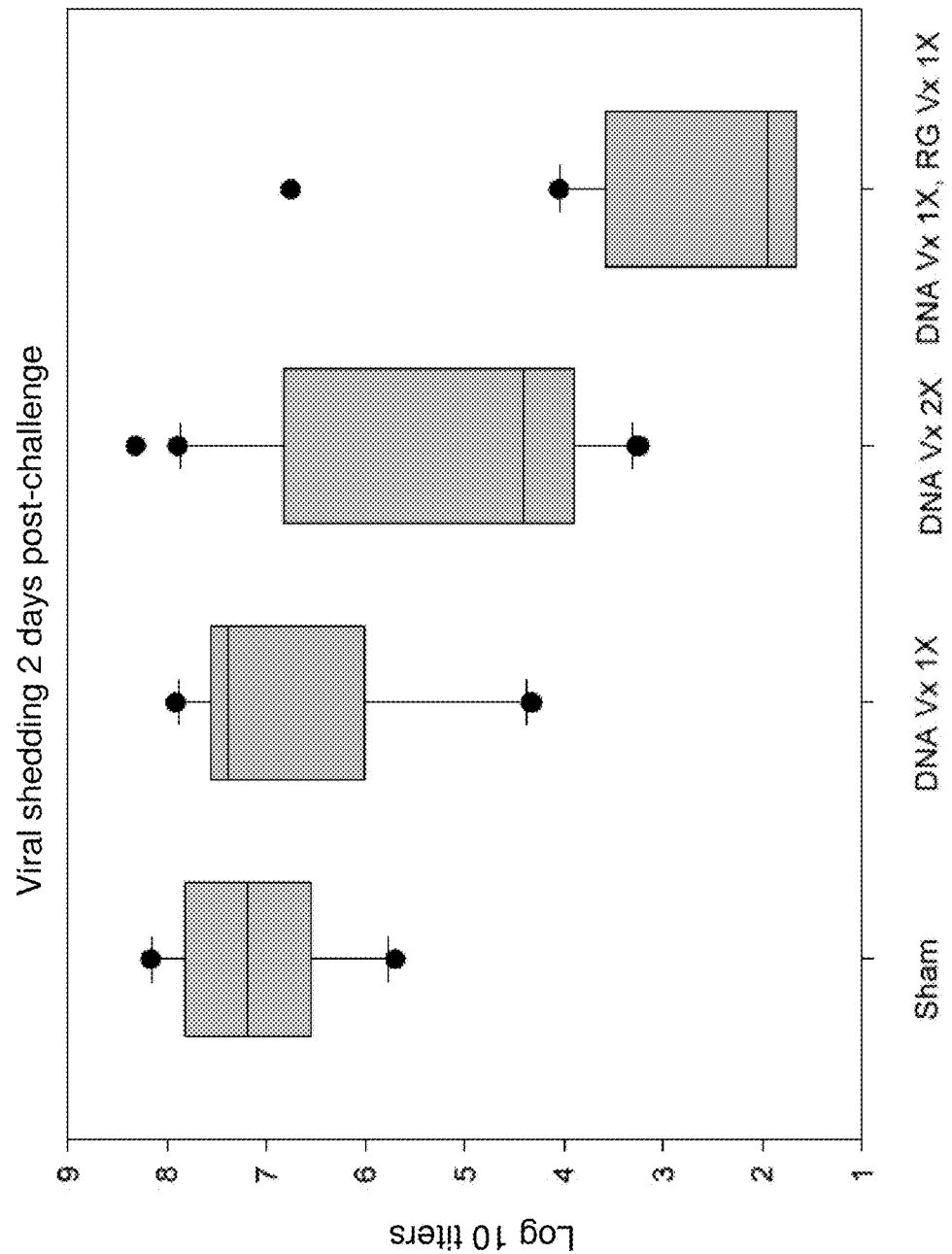

Specification includes a Sequence Listing.

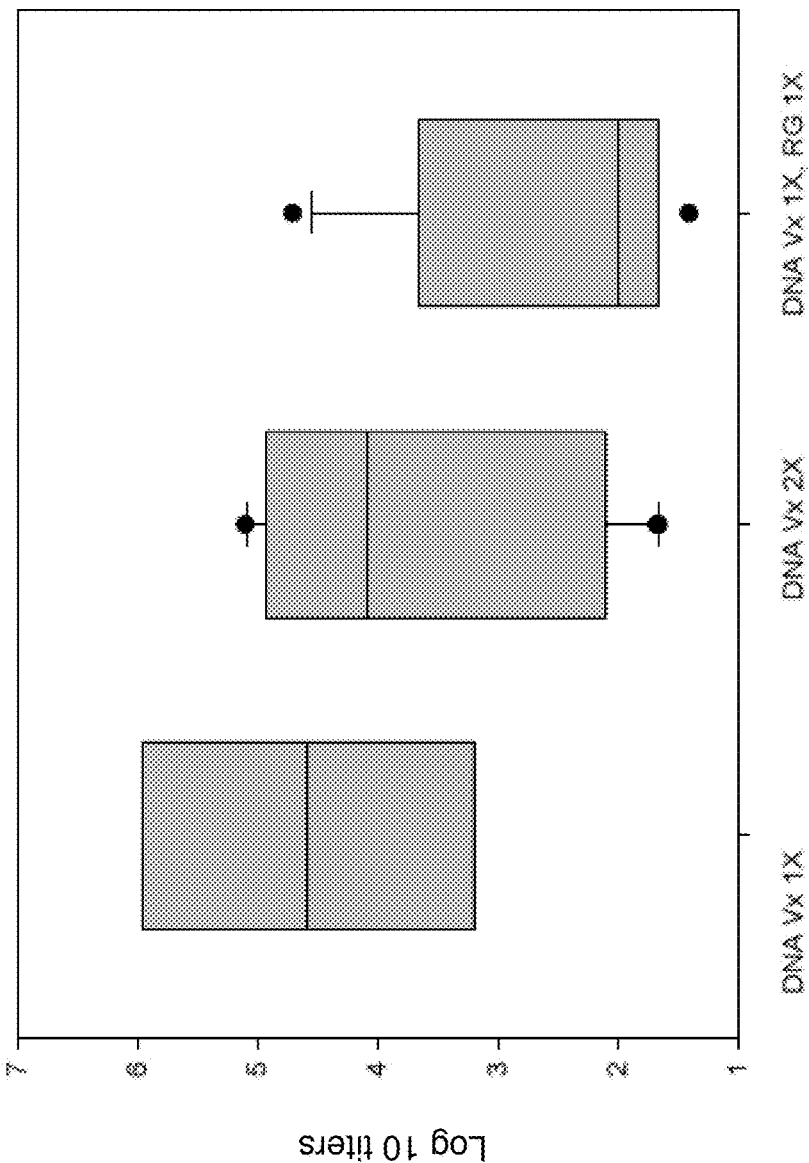

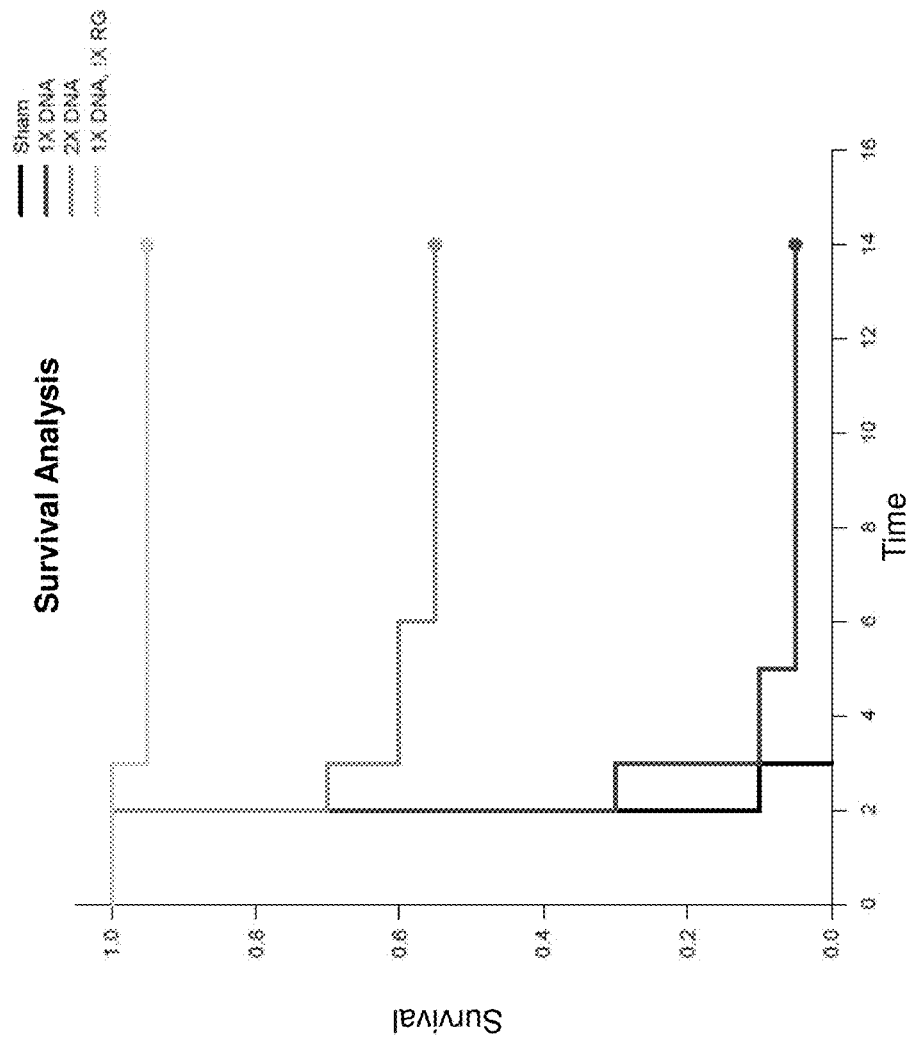

```
                        SEQUENCE LISTING

<160> NUMBER OF SEQ ID NOS: 1

<210> SEQ ID NO 1
<211> LENGTH: 12
<212> TYPE: PRT
<213> ORGANISM: Avian influenza virus
<220> FEATURE:
<221> NAME/KEY: MISC_FEATURE
<223> OTHER INFORMATION: Sequence is a HP multibasic cleavage site

<400> SEQUENCE: 1

Pro Leu Arg Glu Arg Arg Arg Lys Arg Gly Leu Phe
1               5                   10
```

ADJUVANT COMPOSITIONS AND RELATED METHODS

FIELD OF DISCLOSURE

The field of disclosure relates to adjuvant compositions for use in bio-pharmaceutical preparations. The adjuvants are particularly suited to use with bio-pharmaceutical preparations that are absorbed through the skin or injected into the recipient.

BACKGROUND

Adjuvants have the potential to determine or at least influence the success or failure of vaccine compositions. Additionally, adjuvants often determine or augment the administration method of a given antigen. All routes of vaccine administration could benefit from enhanced efficacy and controlled formulation including the ability to use less antigen and still receive the same or better immunogenic response in the animal. Transdermal administration has several advantages compared with other routes of administration due to the ease of administration and a lower amount of stress placed on a recipient. Transdermal administration is advantageous for animals, including pigs, due to the ability of the farmer to easily administer a vaccine to a large group of animals with minimal stress on the animal and the farmer. Needleless administration methods or ways to inoculate other than with the use of needles have become one option for successful administration of large groups of animals without causing undue stress on the animals. This route of administration is also more humane. Transdermal administration is also advantageous for children and the elderly who are routinely resistant to other modes of administration of vaccines. Methods for transdermal administration are becoming more available; however, adjuvants suitable for such administration are not widely available. Further, adjuvant compositions incorporating lecithin are common and these adjuvants are not always suitable for all possible routes of administration and for certain types of antigens when used in different species, including pigs. As with other administration routes, transdermal administration could benefit from enhanced efficacy and controlled formulation as described above. Additionally, all routes of administration including transdermal and injectable vaccines (intravenous (IV), intraperitoneal (IP), intramuscular (IM), and subcutaneous (SC) routes) could all benefit from improved onset to immunity and duration of immunity as well as controlled formulation. What is needed in the art are adjuvant compositions that can be formulated to suit the antigen and route of administration and particularly to those routes of administration that are not as commonly used due to efficacy, such as transdermal. Adjuvant compositions suited for animals that can utilize formulations with components other than lecithin are also needed in the art. Finally, compositions with improved capability such as onset and duration of immunity that do not incorporate lecithin are also needed in the art.

SUMMARY OF DISCLOSURE

The present disclosure overcomes the problems inherent in the prior art and provides for adjuvant compositions and vaccine compositions suitable for use in animals, including pigs. The present disclosure additionally provides for methods related to such adjuvant and vaccine compositions. The adjuvant compositions of the present disclosure are also especially suited for use with pharmaceutical preparations which are absorbed through the dermis and further enhance preparations used in conventional routes such as intravenous (IV), intraperitoneal (IP), intramuscular (IM) and subcutaneous (SC). The adjuvants of the present invention are also especially useful in needleless administration techniques. Further, in some preferred forms, they do not include lecithin.

The adjuvant compositions of the present disclosure are particularly suited to needleless administration techniques, such as transdermal delivery, because they permit or enhance the capability of antigens which normally have difficulty being absorbed transdermally to be absorbed through the skin of the recipient. This has several advantages in animals, including less stress on the animal for vaccination. With regard to humans, this is advantageous in use with children and elderly patients who may resist other types of administration routes. Vaccine formulations that allow rapid dissemination from the site but have ability to absorb to circulating cell populations have an advantage of reducing bruising and condemnation of meat at the slaughter house. The present disclosure provides for a better use of conventional routes of vaccination due to the composition of the adjuvant compositions. The adjuvant compositions of the present disclosure generally include the use of a lipophile, with a preferred lipophile being a composition commercially known as LABRAFAC™ (Gattefossé, Lyon, France).

The adjuvant compositions of the present disclosure preferably provide for 0.1% to 80% higher absorption of or reaction to antigens, both as an injectable composition when administered with or combined with an antigen and via the skin when administered with or combined with an antigen. More preferably, the absorption or reaction is about 1% to 80% higher, where ranges and values such as 1% to 80%, 5% to 60%, 10% to 70%, 2% to 18%, 20% to 45%, 5% to 65%, 0.1% to 35%, 0.5%, 3%, 4%, 5%, 6%, 7%, 8%, 9%, 10%, 11%, 12%, 13%, 14%, 15%, 16%, 17%, 18%, 19%, 20%, 25%, 27%, 30%, 32%, 35%, 37%, 40%, 42%, 45%, 47%, 50%, 52%, 55%, 58%, 60%, 62%, 65%, 67%, 70%, 72%, 75%, 78%, and 80% are envisioned. All values of higher absorption of or reaction to the antigens via the skin or as an injectable are when compared to other adjuvant compositions combined with or administered with the same antigen.

When combined with an antigen such as in a vaccine, the adjuvant compositions of the present disclosure provide improved presentation of the antigen portion of the vaccine to the immune system of the recipient of the vaccine. Such improved presentation is in comparison to the same antigen when combined with an adjuvant composition that is not part of this disclosure. Preferably, the improved presentation permits the use of smaller or lower amounts of antigen to achieve the same level of immune system reaction. The level of immune system reaction can be measured by the strength of the response, as measured by markers of immune response including clinical signs (such as the reduction of the severity and incidence of clinical signs of infection) and biological markers (such as serology), or can be measured by the duration of immunity or protection, or combinations of these indicators of immune system reaction. Even more preferably, the improved antigen presentation permits the use of 95% of the amount of antigen, more preferably 90%, still more preferably 85%, 80%, 75%, 60%, 65%, 60%, 55%, 50%, 45%, 40%, 35%, 30%, 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009, 0.008%, 0.007%, 0.006%, 0.005%, as well as ranges formed by any two members of this group, to achieve the same level of immune system reaction as the same antigen in combination with a different adjuvant when administered to an animal of the same species.

A further advantage of the adjuvant compositions of the present disclosure and related methods are that they do not include lecithin as lecithin has been shown not to be useful for all antigen types. The adjuvant composition of the present disclosure preferably provides effective adjuvant compositions and related methods which do not utilize lecithin and have been shown to provide enhanced immune response for antigens and/or animals that lecithin does not induce or provide an immune response against or for.

The adjuvant composition of the present disclosure generally comprises a lipophile, a polymer of acrylic or methacrylic acid, saline, cholesterol, alcohol, a saponin, and sodium hydroxide. The adjuvant composition has been shown to work for needleless administration, dermal administration, and other routes of administration.

Advantageously, the adjuvant composition of the present disclosure is neither virucidal nor cytotoxic, meaning that the adjuvant composition does not degrade the antigen, making it ineffective to induce an appropriate immune response in a recipient. The adjuvant can be used to screen antigens in vitro. Preferably, the virucidal activity of the adjuvant has a tissue culture EID50 when the lipid concentration is less than 5% lipid. Cytotoxic effects on cell culture vary depending on the cell culture used, but a safe range can be from 0.025% to 5%. Preferred ranges are less than 5%, more preferably less than 4%, still more preferably between 0.25% to about 3%, even more preferably between about 0.25%

A method of making the adjuvant composition of the present disclosure is also provided. The method preferably includes the steps of combining the components of the adjuvant composition and adding a neutralizing agent. The step of combining the components of the adjuvant composition preferably includes at least one emulsion.

The present disclosure further provides for a vaccine composition comprising the adjuvant composition of the present disclosure and an antigen. The antigen can be any antigen suitable for use as an immunogenic composition or vaccine. Preferably, the ratio of the adjuvant of the present disclosure to the antigen is about 1:20, 1:17, 1:15, 1:12, 1:10, 1:9, 1:8, 1:7, 1:6, 1:5, 1:4, 1:3, 1:2, and 1:1.5 with 1:5 being particularly preferred.

A method of vaccinating an animal or human is also provided. The steps of the method preferably include administering the vaccine composition of the present disclosure to a recipient in need thereof. The vaccine can be administered via needleless administration or injected. The recipient is preferably a human or animal, where the animal is selected from, but is not limited to, cows, pigs, horses, dogs, cats, mules, sheep, monkeys, companion animals and other mammals. In one embodiment, the vaccine composition can be administered via a variety of needleless administration methods. Needleless administration methods include, but are not limited to, vaccine guns, transdermal patches, aerosols, mucosal administration methods, skin adhesion methods, dry particle projectiles, wet projectiles, gold/inert particle guns, and pneumatic guns.

All reference to "comprises" or "comprising" in the present disclosure shall also provide the basis for a "consisting essentially of" or "consisting of" claim language. For example, if the present disclosure provides that the composition comprises A and B, it is understood that the composition can also consist essentially of A and B, or even consist of A and B and each of these are fully disclosed as if they were specifically written for each portion of the disclosure. Each of these terms shall be accorded their usual meaning when used in the preamble of a claim.

DESCRIPTION OF FIGURES

FIG. 1: Scatter plot of oropharyngeal shedding from vaccinated and control birds at 2 days post-challenge;

FIG. 2: Scatter plat of oropharyngeal shedding from vaccinated and control birds at 2 days post-challenge; and FIG. 3: Survival plot for the animals in the investigation outlined in Example 5.

DETAILED DESCRIPTION

The adjuvant composition of the present disclosure preferably comprises a lipophile and a polymer of acrylic or methacrylic acid or any particle type component. In other embodiments, the adjuvant composition further comprises at least one of the following: saline, immunomodulators, small molecules, cytokines, sterols including cholesterol, alcohol, a saponin, and sodium hydroxide.

The lipophile can be any lipophile having medium chain triglycerides. Preferably, the lipophile is selected from the group consisting of medium chain EP triglycerides, medium chain triglycerides NF, medium chain fatty acid triglyceride JPE, caprylic/capric triglyceride, and combinations thereof. In a particularly preferred embodiment, the lipophile is LABRAFAC™ (Gattefossé, Lyon, France).

In a preferred embodiment, the lipophile is present in the adjuvant composition of the present disclosure in an amount from about 0.01% to about 5% of the total volume of the composition, where amounts including 0.1% to 4.7%, 0.2% to 4.5%, 0.3 to 4.4%, 0.5% to 4.3%, 0.7% to 4.2%, 0.9% to 4.1%, 1% to 4%, 2% to 4%, 2% to 5%, 3% to 5%, 0.1%, 0.2%, 0.3%, 0.4%, 0.5%, 0.6%, 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, 3.0%, 3.2%, 3.4%, 3.5%, 3.8%, 4%, 4.2%, 4.5%, 4.8%, and 5% by volume and all ranges from any two points therebetween are envisioned. In a particularly preferred embodiment, the lipophile is present in an amount of about 1.8% by volume.

The polymer of acrylic or methacrylic acid compound is preferably selected from the polymers of acrylic or methacrylic acid and the copolymers of maleic anhydride and alkenyl derivative. Examples of such compounds include the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL™; (BF Goodrich, Ohio, USA) are particularly appropriate. They are cross-linked with an allyl sucrose or with allyl pentaerythritol. There are a variety of CARBOPOL™ products which would be suitable for use with the present disclosure. One particularly preferred product for use is CARBOPOL™ 974 P NF Polymer.

In a preferred embodiment, the polymer of acrylic or methacrylic acid is preferably present in the adjuvant composition of the present disclosure in an amount of from about 0.1% to about 3.0% by volume, where values such as 0.1% to 1%, 0.1% to 1.5%, 0.5% to 1%, 0.5% to 2%, 0.5% to 3%, 0.2%, 0.3%, 0.4%, 0.5%, 0.6%. 0.7%, 0.8%, 0.9%, 0.94%, 0.95%, 0.96%, 0.97%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. In a particularly preferred embodiment, the polymer of acrylic or methacrylic acid is present in an amount of about 0.9% by volume.

The saline component can be any solution of sodium chloride and water suitable for use in an adjuvant composition. Typically, saline refers to a solution of 0.90% w/v of NaCl, about 300 mOsm/L or 9.0 g per liter, however, saline for purpose of the present disclosure is not limited to this solution. In a particularly preferred embodiment, the saline solution is Dulbecco's Phosphate Buffered Saline without Calcium or Magnesium (Cellgro Catalog No. 21-CV).

In a preferred embodiment, the saline solution is present in an amount of from about 50% to 98% of the adjuvant composition of the present disclosure by volume, where amounts such as 60% to 98%, 70% to 98%, 80% to 98%, 90% to 98%, 55%, 60%, 65%, 70%, 75%, 80%, 85%, 86%, 87%, 88%, 89%, 90%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 94%, 95%, 96%, 97%, and 98% are envisioned. In a particularly preferred embodiment, saline is present in the adjuvant composition of the present disclosure in an amount of about 92% by volume.

The alcohol component is preferably selected from the group consisting of ethanol, isopropanol, butanol, and combinations thereof. In a preferred embodiment, ethanol is used. Preferably, the ethanol is a 90% to 100% solution, however, ethanol solutions from 10% to 90% could also be utilized for purposes of the present disclosure.

In a preferred embodiment, the alcohol is present in an amount of from about 0.01% to 3% of the adjuvant composition of the present disclosure, by volume, where values such as 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.6%. 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. Further, ranges incorporating any two of the described values are also envisioned. For example, 0.01% to 1%, 0.01% to 2%, 0.3% to 1%, 0.3% to 1.5%, 0.03% to 0.07%, 0.05% to 2.4%, and 1% to 1.6% are all covered in by the present disclosure. In a particularly preferred embodiment, the alcohol is present in the adjuvant composition of the present disclosure in an amount of about 0.05% by volume. The alcohol is useful for solubilizing the saponin, preferably Quil A and much or most (at least 10%, 20%, 30%, 40%, 50%, 60%, 70%, or more) dries off leaving the final concentration of the alcohol in the final product very low.

The saponin for purposes of the present disclosure can be any selected from the class of saponins. Generally, saponins are a class of chemical compounds found in particular abundance in various plant species. Preferably, they are amphipathic glycosides grouped phenomenologically by the soap-like foaming they produce when shaken in aqueous solutions, and structurally by having one or more hydrophilic glycoside moieties combined with a lipophilic triterpene derivative. In a preferred embodiment, the saponin is purified or semi-purified and lyophilized. Preferably, the saponin is an extract from the cortex of the South American tree, Quillaja saponaria Molia. Most preferably, the saponin is Quil A.

In a preferred embodiment, the saponin is present in the adjuvant composition of the present disclosure in an amount of about 0.001% to about 0.5%, where values such as 0.001%, 0.002%, 0.003%, 0.004%, 0.005%, 0.006%. 0.007%, 0.008%, 0.009%, 0.01%, 0.015%, 0.02%, 0.025%, 0.03%, 0.035%, 0.04%, 0.045%, 0.05%, 0.06%, 0.07%, 0.08%, 0.09%, 0.1%, 0.15%, 0.2%, 0.25%, 0.3%, 0.35%, 0.4%, 0.45% and 0.5% are envisioned. Further, ranges including any two discreet values described above are also envisioned. For example, the saponin may be present in the adjuvant composition of the present disclosure in an amount from about 0.003% to 0.01%, 0.003% to 0.05%, 0.01% to 0.03%, 0.1%, to 0.5%, 0.07% to 0.2%, and the like. In a particularly preferred embodiment, the saponin is present in an amount of about 0.009%.

The adjuvant composition of the present disclosure preferably includes a sterol. Any sterol will work for purposes of the present disclosure, including those that occur in plants, animals, and fungi. The sterol is preferably taken from a plant source, however, the sterol may be selected from but not limited to, phytosterols, zoosterols, cholesterol, campesterol, sitosterol, stigmasterol, ergosterol, and combinations thereof. In a particularly preferred embodiment, the sterol is a phytosterol, more preferably cholesterol, preferably of non-animal origin. The cholesterol can be any cholesterol source suitable for use in an adjuvant composition. The cholesterol is preferably derived from animals or plants, most preferably, the cholesterol is plant derived.

In a preferred embodiment, the cholesterol is present in the adjuvant composition of the present disclosure in an amount of from about 0.001% to about 3% by volume, where values such as 0.005% to 0.05%, 0.008% to 0.008%, 0.002%, 0.003%, 0.004%, 0.005%, 0.006%. 0.007%, 0.008%, 0.009%, 0.01%, 0.02%, 0.03%, 0.04%, 0.05%, 0.06%. 0.07%, 0.08%, 0.09%, 0.1%, 0.2%, 0.3%, 0.4%, 0.5%, 0.6%. 0.7%, 0.8%, 0.9%, 1.0%, 1.1%, 1.2% 1.3%, 1.4% 1.5%, 1.6%, 1.7%, 1.8%, 1.9%, 2%, 2.2%, 2.4%, 2.6%, 2.8%, and 3.0% are envisioned. Further, ranges including any two of these volumes are also envisioned. In a particularly preferred embodiment, the cholesterol is present in an amount of about 0.01% by volume.

The adjuvant composition of the present disclosure preferably comprises a component that neutralizes the pH of the composition to a pH from about 6-8, more preferably a pH of 7. Any conventional neutralizer can be use, but preferably, the neutralizer is selected from the group consisting of sodium hydroxide, potassium hydroxide, and ammonium hydroxide. In a particularly preferred embodiment, the component that neutralizes the pH of the solution is sodium hydroxide.

In a preferred embodiment, the component that neutralizes the pH of the adjuvant composition is present in an amount of about 0.1% to 10%, where values such as 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, and 10% are envisioned. Additionally, any range incorporating two of these values is also envisioned including, but not limited to 2% to 8%, 2% to 6%, 3% to 8%, 4% to 6%, 1.5%, 2%, 2.5%, 3%, 3.5%, 4%, 4.5%, 5%, 5.5%, 6%, 6.5%, 7%, 7.5%, 8%, 8.5%, 9%, and 9.5%. In a particularly preferred embodiment, the component that neutralizes the pH of the adjuvant composition is present in an amount of about 5% by volume.

In another embodiment of the present disclosure, the adjuvant composition comprises LABRAFAC™, cholesterol, and Quil-A. In an additional embodiment, the adjuvant composition of the present invention comprises LABRAFAC™, CARBOPOL™, Saline, Cholesterol, Ethanol, Quil-A and Sodium Hydroxide. In yet a further embodiment, the adjuvant composition of the present disclosure comprises LABRAFAC™, CARBOPOL™ 974 P, Saline, vegetable-derived Cholesterol, Ethanol, Quil-A, and Sodium hydroxide. In another embodiment, the adjuvant composition of the present disclosure comprises about 2% LABRAFAC™, by volume, about 1.0% CARBOPOL™, by volume, about 92% Saline, by volume, about 0.01% Cholesterol, by volume, about 0.5% Ethanol, by volume, about 0.09% Quil-A, by volume, and about 5% Sodium hydroxide.

A method of making the adjuvant composition of the present disclosure is also provided. In one form of the method, the method preferably comprises the steps of combining the components of the adjuvant composition, preferably via emulsion, and adding a composition that neutralizes the pH of the adjuvant composition.

In a further embodiment of the present disclosure, the method for making the adjuvant composition of the present disclosure comprises the steps of admixing a lipophile, polymer of acrylic or methacrylic acid, and saline to form a composition. A further embodiment of the present disclosure additionally provides for the step of performing at least one emulsion before the pH of the first composition is adjusted.

The present disclosure also provides for a vaccine composition. The vaccine composition preferably comprises the adjuvant composition of the present disclosure and an antigen(s). The amount of the adjuvant composition of the present disclosure and the amount of antigen, as well as the antigen production technology depend on the administration method selected. Those of skill in the art will be able to determine the appropriate ratio for such administration methods. Preferably, the adjuvant composition is present in an amount of from about 1% to 30%, by volume, of the total volume of the vaccine composition, where values and ranges such as 1% to 25%, 1% to 20%, 1% to 15%, 15% to 30%, 10% to 20%, 10% to 25%, 10% to 20%, 15% to 25%, 20% to 30%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, and 30% are envisioned. In a particularly preferred embodiment, the adjuvant composition is present in an amount of about 20% by volume. In an alternate embodiment, the ratio of the adjuvant composition of the present disclosure to the amount of antigen in the vaccine composition is as disclosed above, and preferably 1:5.

Preferably, the adjuvants of the present invention are shelf-stable alone or when admixed with one or more antigens. Preferably, the shelf life of the adjuvant of the present invention is shelf stable for at least 4 months, more preferably, for at least 5 months, more preferably, for at least 6 months, for at least 12 months, for at least 18 months, and for at least 24 months, for at least 36 months where ranges such as 6-18 months, 6-24 months, 6-36, 12-24 months, 12-36 months, 18-24 months, and 18-36 months are envisioned. Preferably, the adjuvants of the present invention are shelf stable for these durations at ambient temperatures. Preferably, the temperature range is about 16-26° C.

The present disclosure additionally provides for a method of vaccinating animals or humans. The method preferably comprises the step of administering the vaccine composition of the present disclosure to a recipient thereof. Alternatively, the method of the present disclosure comprises the steps of combining the adjuvant of the present disclosure with an antigen to form a composition and administering the composition to an animal or human in need thereof. Preferably, the antigen is one typically utilized in an immunogenic composition or vaccine composition and is preferably capable of providing an immune response in the recipient. The recipient is preferably a human or animal. In an embodiment where the recipient is an animal, the animal is preferably selected from the group consisting of pigs, cows, horses, dogs, cats, sheep, mules, monkeys, companion animals, and other mammals.

The antigen, for purposes of the vaccine composition of the present disclosure, can be any antigen or combination of antigens suitable to induce an immunogenic response in a recipient. The recipient may be an animal or a human. The antigen for use in this invention may be any desired antigen falling within the definition set forth above. Antigens are commercially available or one of skill in the art is capable of producing them. In some preferred forms, the antigenic moiety making up the vaccine can be either a modified-live or killed microorganism, or a natural product purified from a microorganism or other cell including, but not limited to, tumor cell, a synthetic product, a genetically engineered protein, peptide, polysaccharide or similar product, or an allergen. The antigenic moiety can also be a subunit of a protein, peptide, polysaccharide or similar product. The antigen may also be the genetic antigens, i.e., the DNA or RNA that engenders an immune response. Representative of the antigens that can be used according to the present invention include, but are not limited to, natural, recombinant or synthetic products derived from viruses, bacteria, fungi, parasites and other infectious agents in addition to autoimmune diseases, hormones, or tumor antigens which might be used in prophylactic or therapeutic vaccines and allergens. The viral or bacterial products can be components which the organism produced by enzymatic cleavage or can be components of the organism that were produced by recombinant DNA techniques that are well known to those of ordinary skill in the art. Because of the nature of the invention and its mode of delivery it is very conceivable that the invention would also function as a delivery system for drugs, such as hormones, antibiotics and antivirals. Examples of antigens suitable for use in the vaccine composition of the present disclosure, include, but are not limited to antigens derived from Porcine Reproductive and Respiratory Syndrome (PRRS); *Mycoplasma hyopneumoniae* (*M hyo*); Porcine proliferative enteritis; Bovine Viral Diarrhoea Virus (BVD); Border's Disease, Leptospirosis; Brucellosis caused by bacteria of the genus *Brucella; Clostridium*; Tetanus toxemia, caused by a specific neurotoxin produced by *Clostridium tetani; Salmonella* spp; *Escherichia coli*; Swine Pox; Eperythrozoonosis; Classical Swine Fever (CSF) or African Swine Fever (ASF); Pneumonic pasteurellosis and Streptococci, caused by *Pasteurella multocida* and various species of streptococci, typically *S. suis*; Streptococcal meningitis; Pseudorabies; Swine Influenza Virus; Spirochaetal colitis, caused by the Brachyspira pilosicoli bacteria; Swine dysentery, caused by the bacteria Brachyspira hyodysenteriae; coronavirus; Porcine Parvovirus; *Actinobacillus* pleuropneumonia; Glässers Disease, caused by the bacterium *Haemophilus* parasuis (Hps); Exudative epidermitis, caused by the bacterium *Staphylococcus hyicus*; Swine erysipelas, caused by a bacterium, Erysipelothrix rhusiopathiae; Eperythrozoonosis (Epe), caused by a bacterium called Eperythrozoonosis *suis*; Encephalomyocarditis; Herpes Virus; Porcine Cytomegalovirus Infection (PCMV), caused by a herpes virus; Japanese B Encephalitis Virus (JE); Porcine Epidemic Diarrhoea (PED), caused by a coronavirus; Porcine Respiratory Corona Virus Infection (PRCV); Rotavirus; Rabies; Swine Vesicular Disease (SVD); Tuberculosis, caused by *Mycobacterium tuberculosis*; virus of vesicular exanthema of swine (VES); Vesicular Stomatitis (VS) virus; and Eastern equine encephalomyelitis viruses (EEEV). As understood by those of skill in the art and the usefulness of the vaccine with any type of antigen, all variations of the antigen including whole organisms, macromolecules, subunits, nucleic acids, expressed proteins, and combinations thereof are contemplated by the present disclosure.

The method of vaccinating of the present disclosure preferably includes administration of the composition comprising the adjuvant of the present disclosure and an antigen, where administration is needleless or through injection. More preferably, the administration method is selected from the group consisting of topical, intramuscular, nasal, oral, transdermal, mucosal, and subcutaneous. The adjuvant composition of the present disclosure provides for an advantage in needleless administration methods, where the administration utilizes skin-absorption of antigens, therefore, in a preferred embodiment, the administration method is transdermal or mucosal. In a further embodiment, the administration for purposes of the method of the present disclosure is via a needleless administration method, such as a vaccine gun; however, the method of the present disclosure is not limited to this embodiment. The present invention is not limited to vaccine guns, as any needleless administration method will work. Needleless administration methods include, but are not limited to, vaccine guns, transdermal patches, aerosols, mucosal administration methods, skin adhesion methods, dry particle projectiles, wet projectiles, gold/inert particle guns, and pneumatic guns.

Further, the present disclosure provides for a method of administering a vaccine composition to a pig. The method preferably includes the step of combining the adjuvant composition of the present disclosure with an antigen and administering the vaccine composition via transdermal delivery to a pig in need thereof. In a particularly preferred embodiment, the method includes the step of delivering the vaccine composition of the present disclosure to a pig via vaccine gun administration.

The adjuvant composition of the present disclosure is particularly suited to transdermal delivery because it allows antigens which normally have difficulty being absorbed transdermally to be absorbed through the skin or dermis of the recipient. The adjuvant of the present disclosure preferably provides for 0.001% to 80% higher absorption of antigens via the skin, when compared to other adjuvant compositions.

It should be understood that every maximum numerical limitation provided in the specification includes every lower numerical limitation as if it were expressly written herein. Every minimum numerical limitation provided in the specification includes every higher limitation as if it were expressly written herein. Every numerical range provided herein expressly includes every narrower numerical range that falls within the broader numerical range, as if such narrower numerical range was expressly written herein.

The composition and methods disclosed in the present application can comprise, consist essentially of, or consist of the essential elements and limitations of the invention described herein, as well as any optional or additional ingredients, components, steps, or limitations described herein or otherwise useful in compositions and methods such as those described herein.

EXAMPLES

Example 1

This example illustrates the method of production for an adjuvant exemplary of those provided by the present disclosure.

Materials and Methods

The Materials used were as follows:

A. LABRAFAC™ Lipophile WL1349 (Gattefossé Catalog No. 3139)

B. CARBOPOL® 974P NF Polymer (Lubrizol Catalog No. CBP974PNF)

C. Dulbecco's Phosphate Buffered Saline without Calcium or Magnesium (Cellgro Catalog No. 21-031-CV) or equivalent D. Cholesterol, Plant-Derived, (Avanti Catalog No. 700100P)

E. Ethanol, 100% Solution, (Acros Catalog No. 61509-0010) or equivalent

F. Quil-A, (Brenntag Catalog Purified Saponin Quil-A, Lyophilized)

G. 5N Sodium hydroxide, (VWR Catalog No. BDH3225-1) or equivalent

TABLE 1

Formulation of Adjuvant 06 Stock

| Ingredient | Amount Required to Prepare 10,000 mL |
|---|---|
| Gattefossé-LABRAFAC ™ Lipophile WL1349 | 198 mL |
| CARBOPOL ® 974P NF Polymer | 100.0 g |
| Dulbecco's Phosphate Buffered Saline without Calcium or Magnesium | Q.S. 10,000 mL |

Cholesterol Stock

| Ingredient | Amount Required |
|---|---|
| Cholesterol, Plant-Derived | 1.8 g |
| Ethanol, 100% Solution | 100 mL |

A cholesterol stock was then prepared by adding the cholesterol to ethanol. It was then mixed until dissolved. The solution was then sterile-filtered using a 0.2 µm filter. The solution was then stored at 2-7° C.

Quil-A Stock

| Ingredient | Amount Required |
|---|---|
| Quil-A Saponin | 1.25 g |
| Reverse-Osmosis/Deionized (RO/DI) Water | 25 mL |

Next, a Quil-A stock was prepared by adding Quil-A Saponin to RO/DI water where it was mixed until dissolved. The solution was then sterile-filtered using a 0.2 µm filter. Next, the solution was stored at 2-7° C. The stock was a 4% as a 5× stock for Quil-A.

Preparation of Adjuvant 06

A 1:5 dilution of the Quil A stock was prepared, using the adjuvant 06 stock, by adding 20 mL of Quil A to 80 mL of adjuvant 06 stock and it was mixed by swirling. Next, 56 mL of Cholesterol stock was added to the bulk adjuvant 06 stock. Then 100 mL of the 1:5 dilution of the Quil A was added to the remaining bulk adjuvant 06 stock that now contained 56 mL of the cholesterol stock. The adjuvant mixture was then mixed for approximately 15 minutes. While it was being mixed, the adjuvant was aseptically aliquoted into sterile 60 mL PETG bottles at 50 mL aliquots. Each bottle was then sealed with a screw top cap. The bottles of Adjuvant 06 were then stored for not more than two years at 2-7° C.

Instructions for Use

The amount of Adjuvant 06 was calculated to mix with the antigen; using 1 part Adjuvant 06 with 4 parts antigen. This was also done at a 1:9 ratio. However, it could easily be done using a 1:10 or 1:20 ratio.

The container of Adjuvant 06 should be mixed thoroughly before use. A small amount of Adjuvant 06 was aseptically drawn up with a sterile syringe and 18 gauge needle, and then evacuated to remove all air from the syringe. The desired amount of Adjuvant 06 was then steadily pulled up into the syringe. The measured volume of Adjuvant 06 was then added to the antigen and mixed thoroughly.

Example 2

The purpose of this study was to determine whether two different adjuvant formulations, each separate embodiments of the present disclosure, could be tested in mice when diluted to the concentration intended for use with vaccines.

Materials and Methods

Two killed K99 *E. coli* vaccines, one adjuvanted and one prepared in PBS, were also included in the study to determine whether the addition of an antigen would have a different effect on the mice compared to the same adjuvant formulation tested alone.

Adult female CF-1 mice approximately 6 weeks in age with an average weight of 27 g were inoculated with 0.5 ml of each of the five different adjuvant formulations diluted to a final 1× concentration. Mice were also inoculated with 0.5 ml of each killed K99 *E. coli* vaccine. The adjuvant used to prepare the adjuvanted killed K99 *E. coli* vaccine is the same formulation as catalog number 70X0106, which contains the highest concentration of all ingredients for that formulation. Each treatment group consisted of eight mice inoculated either by subcutaneous injection in the back of the neck or by intraperitoneal injection. All mice were housed for seven days post-inoculation and observed for health.

All mice inoculated via subcutaneous injection in the back of the neck appeared to be healthy seven days post-inoculation, however three of the eight mice given the adjuvanted killed K99 *E. coli* vaccine exhibited lesions at the injection site by day 7 of the study. At least six of the eight mice in each group inoculated via intraperitoneal injection died between 24 and 48 hours post-inoculation.

Animals

Sixty-four female CF-1 mice sourced from Charles River Laboratories were approximately 6 weeks (44 days) old at the time of test article administration. Upon receipt the mice weighed an average of 19 grams. The mice were weighed again prior to test article administration on day 0 and weighed an average of 27 grams.

Test Articles

Adjuvants

VaxLiant Catalog 70X0005-5x, Lot 00003, Exp. 7 Oct. 2015

VaxLiant Catalog 70X0106-5x, Lot 00003, Exp. 7 Oct. 2015

Dulbecco's Phosphate Buffered Saline (DPBS); Cellgro, catalog: 21-031-CV Lot: 21031439 Exp. 30 Sep. 2016

Killed K99 *E. coli* Vaccines

Vaccine containing Adjuvant C VaxLiant Catalog Number 708101, Killed *E. coli* expressing K99 pili-Lot K9928Dec12A Vaccine containing PBS, Killed *E. coli* expressing K99 pili-Lot K9928Dec12B Methods Study Time Line

TABLE 2

Study Time Line

| Date | Day of Study | Description |
|---|---|---|
| 3 Feb. 2014 | −44 | Birth date |
| 12 Mar. 2014 | −7 | Receipt of mice at animal facility |
| 19 Mar. 2014 | 0 | Treatment administration to all groups |
| 26 Mar. 2014 | 7 | End of study |

Study Design

TABLE 3

Study Design

| Treatment Group | Treatment Description | Number of Animals | Route of Inoculations[1] | Days Observed for Health |
|---|---|---|---|---|
| T01 | Adjuvant 70X0005 | 8 | SC | 0-7 |
| T02 | Adjuvant 70X0106 | 8 | SC | 0-7 |
| T03 | Killed K99 + Adjuvant C (ENABL C1) | 8 | SC | 0-7 |
| T04 | Killed K99 + PBS | 8 | SC | 0-7 |
| T05 | Adjuvant 70X0005 | 8 | IP | 0-7 |
| T06 | Adjuvant 70X0106 | 8 | IP | 0-1 |
| T07 | Killed K99 + Adjuvant C (ENABL C1) | 8 | IP | 0-1 |
| T08 | Killed K99 + PBS | 8 | IP | 0-7 |

[1]SC-Subcutaneous injection in back of neck; IP = Intraperitoneal injection

Animal Receipt, Acclimation and Randomization

Upon receipt, mice were weighed five at a time, and each mouse was placed into a separate cage. This process was repeated until there were four mice placed per cage.

Daily health observations were performed during the seven day acclimation period.

Cages 1-16 were randomly assigned to treatment groups T01-T08 by drawing two cage numbers from a container and assigning them to group T01. The next two cage numbers drawn were assigned to group T02 and so on until all cages were assigned to a treatment group. See Table 4 for the cage numbers assigned to each treatment group.

TABLE 4

Cage Number Assigned to each Treatment Group

| Treatment Group | Treatment Description | Number of Mice per Cage | Cage Numbers |
|---|---|---|---|
| T01 | Adjuvant 70X0005 | 4 | 1, 18 |
| T02 | Adjuvant 70X0106 | 4 | 12, 14 |
| T03 | Killed K99 + Adjuvant C (ENABL C1) | 4 | 4, 11 |
| T04 | Killed K99 + PBS | 4 | 21, 27 |
| T05 | Adjuvant 70X0005 | 4 | 2, 22 |
| T06 | Adjuvant 70X0106 | 4 | 5, 28 |
| T07 | Killed K99 + Adjuvant C (ENABL C1)) | 4 | 7, 17 |
| T08 | Killed K99 + PBS | 4 | 9, 15 |

Test Article Preparation

All test article preparation was performed aseptically on the day of administration.

Adjuvant Preparation

The bottle of the appropriate 5× adjuvant stock was allowed to warm to room temperature and then inverted a minimum of 30 times to mix. The appropriate adjuvant was diluted 1:5 with DPBS (4 parts DPBS+1 part adjuvant) and mixed by inverting a minimum of 30 times. The prepared test article was aliquoted into two separated sterile 5 ml transport tubes and labeled for the appropriate treatment groups.

Killed K99 Vaccines

The Killed K99+PBS vaccine was prepared on 28 Dec. 2012 and stored at 2-7° C. prior to use in this study. The vaccine bottles were allowed to warm to room temperature and then inverted to mix before the material was removed directly from the vaccine vial to inoculate the appropriate treatment groups.

Treatment Administration

Mice were examined for health before administration of the test articles. Two cages of mice, eight mice total, were administered 0.5 ml of each test article. The subcutaneous (SC) injection was administered in the back of the neck using either a 25 g, ⅝" or a 25 g, 1" needle with 3 ml syringe. The intraperitoneal (IP) injection was administered using a 25 g, ⅝" needle with a 3 ml syringe. All treatment administration and time was recorded.

Weights

The mice were weighed using a bench top balance upon receipt in groups of 5 and the average weight of that group was determined.

Just prior to Day 0 (test article administration) the weight per mouse was determined using the same balance as upon receipt. Each cage was weighed. The value recorded for that cage was divided by the number of mice in that cage (4). The reported value was the cage average.

Health Observations

Health observations of the mice were performed at least once per day through day 7 of the study. All health observations were recorded.

Mice were observed for health approximately 82-89 minutes after the last test article was administered for the day 0 observations.

Measurable Criteria

The primary variable or outcome was the presence/absence of adverse events during the 7 day study attributable to the test article. This variable was determined for each adjuvant and route of administration. There were two observations recorded:

Site injection adverse events: lesions observed during the 7 day in-life stage at the site of injection were recorded.

Mortality: mortality was recorded if a mouse was found dead or was culled due to morbidity.

Results and Conclusions

The average weight of all the mice at the time of test article administration was 26.87 g.

Health Observations

None of the mice inoculated via SC injection with any of the adjuvants or the killed K99+PBS vaccine demonstrated an adverse reaction through the 7-day study period. At least six of the eight mice in each group inoculated via IP injection with any of the adjuvants died within 24 to 48 hours post-inoculation. Only the mice inoculated via IP injection with the killed K99+PBS vaccine remained healthy during the 7-day study period. Table 5 shows the mice that died during the study.

TABLE 5

Summary of Mouse Deaths During the Study

| Treatment Group | Description | Average Weight of Mice (g) | Inoculation Route | # Healthy Mice/Total Inoculated 24 hours Post-Inoculation | 7 Days Post-Inoculation |
|---|---|---|---|---|---|
| T01 | Adjuvant 70X0005 | 26.57 | SC | 8/8 | 8/8 |
| T02 | Adjuvant 70X0106 | 26.55 | SC | 8/8 | 8/8 |
| T03 | Killed K99 + Adjuvant C (ENABL C1) | 26.96 | SC | 8/8 | 8/8* |
| T04 | Killed K99 + PBS | 28.14 | SC | 8/8 | 8/8 |
| T05 | Adjuvant 70X0005 | 27.25 | IP | 1/8 | 1/8 |
| T06 | Adjuvant 70X0106 | 26.21 | IP | 0/8 | 0/8 |
| T07 | Killed K99 + Adjuvant C (ENABL C1) | 26.84 | IP | 0/8 | 0/8 |
| T08 | Killed K99 + PBS | 28.57 | IP | 8/8 | 8/8 |

*Mice were healthy throughout study, but had developed lesions at the injection site by day 7.

Discussion

Based on the results of this study, it appears as though vaccines prepared with any of the five adjuvant formulations tested in this study may be able to undergo satisfactory mouse safety testing via 9CFR 113.33 if the final product was administered via SC injection in the back of the neck.

Development of an injection site lesion may be possible when the adjuvant combined with an antigen is administered via this route, however, the lesion is unlikely to result in an unsatisfactory safety test as no other adverse reactions were observed.

However, adverse reactions at the injection site caused by addition of multiple antigens were not examined in this study.

Care was taken to ensure that the mice were above the pre-determined weight of 22 g, but no older than 7 weeks in age.

At least six of the eight mice in each group inoculated via IP injection with adjuvant did not survive more than 48 hours post-inoculation. This indicates that the adjuvants are toxic to the mice when administered in this manner. There is only one common component between the various adjuvant formulations, suggesting that this component may be responsible for the toxicity observed. The toxicity of the adjuvants when administered via IP injection is supported by the lack of adverse reactions in the mice inoculated in the same manner with the killed K99 E. coli vaccine prepared in PBS.

Conclusions

Adjuvanted vaccines prepared with VaxLiant, LLC adjuvant formulations represented by catalogue numbers 70X0005 and 70X0106 may be capable of satisfactory mouse safety results when tested per 9CFR 113.33 if administered via subcutaneous injection in the back of the neck.

Based on the results of this study, all adjuvant formulations diluted to the 1× final concentration appear to be capable of producing a satisfactory result in mouse safety testing when administered via subcutaneous injection to the back of the neck. However, adverse reactions at the injection site are possible when at least one of the adjuvant formulations is tested with an antigen. It is recommended that procedures performed on vaccine final products prepared with any of the two adjuvant formulations tested in this study be conducted by administration via subcutaneous injection in the back of the neck.

Example 3

This example illustrates the efficacy of the claimed adjuvant compositions with an avian flu H5 DNA vaccine.

Materials and Methods 160 male and female pathogen-free chickens were utilized for this study. The Study Design was as follows in Table 6 below.

TABLE 6

| Treatment Group Descriptions | | | | | Blood |
|---|---|---|---|---|---|
| Trt Group [1] | Description | Route [2] | No. of Chickens | Dose (ml) [3] Day | Collections Day |
| T01 | Negative Control (Uninoculated) | N/A | 10 | N/A  0, 14 | 14, 28 |
| T11 | AIV H5 DNA + 1.00X Adjuvant 70X0005 | IM | 10 | 0.4  0, 14 | |
| T12 | AIV H5 DNA + 0.50X Adjuvant 70X0005 | IM | 10 | 0.4  0, 14 | |
| T13 | AIV H5 DNA + 0.25X Adjuvant 70X0005 | IM | 10 | 0.4  0, 14 | |
| T14 | AIV H5 DNA + 1.00X Adjuvant 70X0106 | IM | 10 | 0.4  0, 14 | |
| T15 | AIV H5 DNA + 0.50X Adjuvant 70X0106 | IM | 10 | 0.4  0, 14 | |
| T16 | AIV H5 DNA + 0.25X Adjuvant 70X0106 | IM | 10 | 0.4  0, 14 | |

[1] For this study, the treatment group (TG) designation identifies the chickens and the test article.
[2] IM—Intramuscular injection.
[3] Each chicken will be inoculated with 0.2 ml volume in the left breast muscle and 0.2 ml volume in the right breast muscle.

TABLE 7

| Study Timeline | |
|---|---|
| Day | Activity |
| Prior to Day 0 | Daily Clinical Observations/Acclimation |
| Day 0 | Test Article Administration |
| Day 14 | Blood Collection |
| | Test Article Booster Administration |
| Day 28 | Blood Collection |
| Days 0-28 | Daily Clinical Observations |
| Day 28 | End of Study |

Study Methods

Randomization and Acclimation

Daily health observations for the chickens were recorded on all study birds during the acclimation phase. Birds will be acclimated for a minimum of three days. Clinical observations were performed daily and recorded.

Administration Route

All birds were administered the test articles by intramuscular injection into the left and right sides of the breast.

Test Article Administration—Days 0 and 14

On Day 0 birds were examined for normal health and appearance and enrolled in the study. One cage will represent one treatment group.

The ten birds in T01 were not inoculated to serve as the negative control. The ten birds in each of the remaining treatment groups (T05-T16) were inoculated with the appropriate test article by intramuscular injection on day 0 and day 14 of the study.

Sample Collection and Testing

Blood was collected from each bird on day 14 (prior to the day 14 booster administration of test articles) and day 28 according to site procedures. Blood was allowed to clot and then centrifuged to collect serum. The serum was then stored at −18±5° C. until tested if testing was not going to occur within 48 hours of collection and/or after serum has been tested. Serum was then assayed for the level of seroconversion via Hemagglutination Inhibition Assay (HAI).

Health Observations and Adverse Events

Following administration of the test articles, clinical observations were recorded at least once daily until the end of the study (day 28). All clinical observations were recorded.

Assessment of Results/Data Analysis

Serum samples were assayed for seroconversion via HAI using BBL SOP LP-054. The HAI titer was then determined for each serum sample in each treatment group. The HAI titers of the birds inoculated with 1.00× (20%) adjuvant were then compared to the titers of the birds inoculated with 0.50× (10%) and 0.25× (5%) of each adjuvant formulation to determine which concentration of each adjuvant is most effective Test Article Preparation The Test articles were prepared on the day of administration and transported to the clinical site.

Preparation of the test articles was conducted in bio safety cabinets using aseptic techniques. Final formulations of all test articles were incubated at room temperature for 30±5 minutes prior to administration to birds.

Test Articles

AIV H5 Plasmid DNA Lot Number DNA130414TKWI; Tested for purity and quality.

Dulbecco's Phosphate Buffered Saline (DPBS); Cellgro, catalog: 21-031-CV Lot: 21031439.

TABLE 8

| Adjuvant Stock Identification | | | | | |
|---|---|---|---|---|---|
| Adjuvant Catalog Number | Manufacturer | Lot Number | Expiration Date | LTS Reference [2] | Adjuvant Label Information [3] |
| 70X0005 | BBL | 00003 | 7 Oct. 2015 | LTS-007-00 | Finished Vials Catalog No. 70X0005; Lot No. 00003 Store at 2-7° C./Do not Freeze; NOT FOR USE IN HUMANS; SAMPLE. For Research Only Expiration Date: 7 Oct. 2015 |
| 70X0106 | BBL | 00003 | 7 Oct. 2015 | LTS-006-00 | Finished Vials Catalog No. 70X0106; Lot No. 00003 Store at 2-7° C./Do not Freeze; NOT FOR USE IN HUMANS; SAMPLE. For Research Only Expiration Date: 7 Oct. 2015 |

[2] Reference for BBL SOP QAU-053-01 Attachment II, Lot Testing Summary (LTS)
[3] Each adjuvant 5.00X stock was tested for purity and pH. All of the test articles will be handled aseptically during preparation; final test articles will not undergo further testing

TABLE 9

| Test Article Formulation for each Treatment Group | | | | | |
|---|---|---|---|---|---|
| | Lot Numbers [2] | | | | |
| Trt Group | AIV H5 Plasmid DNA per 0.4 ml dose | 70X0005 | 70X0106 | Day 0 | Day 14 |
| T11 | 30 ug | 1.00X | | NBHO250211ddmmmyy | NBHO250211ddmmmyy |
| T12 | 30 ug | 0.50X | | NBHO250212ddmmmyy | NBHO250212ddmmmyy |
| T13 | 30 ug | 0.25X | | NBHO250213ddmmmyy | NBHO250213ddmmmyy |
| T14 | 30 ug | | 1.00X | NBHO250214ddmmmyy | NBHO250214ddmmmyy |
| T15 | 30 ug | | 0.50X | NBHO250215ddmmmyy | NBHO250215ddmmmyy |
| T16 | 30 ug | | 0.25X | NBHO250216ddmmmyy | NBHO250216ddmmmyy |

[1] Adjuvant stock concentrations are 5.00X. The 1.00X (20%) concentration of the adjuvants is considered the standard concentration.
[2] TBD = To be determined; in the format of: NBHO2502 (treatment group designation) (date of preparation); day 0 and day 14 will be differentiated by the date of preparation.

CaCl precipitation: final concentration of:
Plasmid DNA: 75 ug/mL
Calcium Chloride: 2.68 mM
Sodium Phosphate: 2.68 mM
Sodium Citrate: 0.669 mM Results and Conclusions

TABLE 10

| Results of seroconversion studies | | | | | | |
|---|---|---|---|---|---|---|
| | | Day 14 | | | Day 29 | |
| Group | Description | GMT | No. Seroconverted (N = 10; N = 9*) | GMT seroconverted | GMT | Day 29 No. Seroconverted (N = 10; N = 9*) |
| T01 | Non-treated Control | 2.0 | 0 | 0.0 | 2.0 | 0 |
| T11* | AIV H5 DNA + 1.00X Adj-05 | 3.2 | 3 | 10.0 | 157.6 | 10 |
| T12 | AIV H5 DNA + 0.50X Adj-05 | 2.0 | 0 | 0.0 | 111.4 | 10 |
| T13 | AIV H5 DNA + 0.25X Adj-05 | 3.0 | 2 | 16.0 | 84.4 | 10 |
| T14 | AIV H5 DNA + 1.00X Adj-06 | 3.0 | 3 | 8.0 | 119.4 | 10 |
| T15 | AIV H5 DNA + 0.50X Adj-06 | 2.3 | 1 | 8.0 | 39.4 | 9 |
| T16 | AIV H5 DNA + 0.25X Adj-06 | 2.3 | 1 | 8.0 | 24.3 | 8 |

This study showed that the adjuvants of the present invention are efficacious with the use of DNA-based vaccines.

Example 4

This study illustrates the stability of the adjuvants of the present invention over 18 months.

Materials and Methods

Test Articles

Preparation of Stability Test Articles

Two different adjuvant formulations were combined with BSA for a target concentration of 50 ug BSA (bovine serum albumin)/dose. All test articles prepared were aseptically aliquoted into sterile glass vials with rubber stoppers and crimped shut.

Test article PBO/cold was prepared by aliquoting commercial phosphate buffered saline (PBS) into vials as described and stored at refrigerated temperature. Test articles BSA/PBS/RT and BSA/PBS/cold were prepared by adding 4 parts BSA and 1 part PBS for a target concentration of 500 ug/ml (50 ug/0.1 mL dose) and stored at ambient or refrigerated temperatures. Test articles BSA/Adj01/RT and BSA/Adj01/cold were prepared by adding 4 parts BSA and 1 part Adjuvant 01 for a target concentration of 500 ug/ml (50 ug/0.1 mL dose) and stored at ambient or refrigerated temperatures. Test articles BSA/Adj06/RT and BSA/Adj06/cold were prepared by adding 4 parts BSA and 1 part Adjuvant 06 for a target concentration of 500 ug/ml (50 ug/0.1 mL dose) and stored at ambient or refrigerated temperatures.

Study Methods

Acclimation

Daily health observations were recorded on all study animals during the acclimation phase. Animals were be acclimated for a minimum of six days.

Placement on Test Procedures

Mice were ear notched for identity. Mice were placed in study cages placing five mice per cage. The mice we also weighed during the 6 month testing.

Treatment Administration

Mice were examined for normal health and appearance and enrolled in the study. Mice were maintained according to treatment group with two cages containing five mice each representing a treatment group. The exception was for the mice receiving the placebo (PBO) which consisted of one cage containing five mice.

At the Day 0 time point, regardless of the "storage conditions", one vial of each treatment group was aseptically divided into three aliquots. One aliquot was administered to the mice immediately (Day 0). The second aliquot was stored at 2-7° C. until administered to the mice on Day 14 and was not considered as a "stability" sample. The third aliquot was maintained at 2-7° C. as a retention sample and also not considered a "stability" sample. All test articles were administered to mice subcutaneously dorsal between the shoulders.

Health Observations and Adverse Events

Clinical observations including adverse events were recorded daily until study completion.

Administration Route

All mice will be administered the test article via subcutaneous injection, dorsal between the shoulders.

Prescreen Sample Collection—Day −4-0 (Baseline Mice Only)

Blood was collected and pooled from the baseline mice (the mice not used in the study) once between days −4 and 0 to obtain prescreen serum. No more than 10% of the total blood volume based on the average weight of the mice was collected at this time. Blood was allowed to clot and then centrifuged to collect serum. The serum was be pooled and stored at 2-7° C. or −18±5° C. until tested via ELISA to ensure the mice to be used in the study were seronegative to BSA.

TABLE 11

Treatment Group Descriptions

| Trt Group | Description | Route 1 | No. of Mice | Dose (mL) | Day | Blood Collections Day |
|---|---|---|---|---|---|---|
| T01 | Placebo (PBS only) | SC | 5 | 0.1 | 0, 14 | 13 |
| T02 | 50 ug BSA + PBS | SC | 10 | 0.1 | 0, 14 | 32 |
| T04 | 50 ug BSA + 70X0106 | SC | 10 | 0.1 | 0, 14 | |
| T06 | 50 ug BSA + 70X0105 | SC | 10 | 0.1 | 0, 14 | |

TABLE 12

Summary of Stability Test Articles

| Test Article ID[1] | True Name[2] | Manufacturer | Storage Temp | Volume/Vial (mL) | Number of Vials Prepared | Lot Number | Stability Testing Dates (month) | 6 Month Trt Group |
|---|---|---|---|---|---|---|---|---|
| PBO/cold | S-Placebo (PBS only) | Cellgro (Cat 21-031-CV) | 2-7° C. | 5 | 25 | VACO2376-PBO/cold-21 Nov. 2013 | 0, 6, 12, 18, 24 | T01 |
| BSA/PBS/cold | S-50 ug BSA + PBS | BBL | 2-7° C. | 5 | 26 | VACO2376-BSA/PBS/cold-21 Nov. 2013 | 0, 6, 12, 18, 24 | T02 |
| BSA/PBS/RT | S-50 ug BSA + PBS | | 18-27° C. | 5 | 26 | VACO2376-BSA/PBS/RT-21 Nov. 2013 | 0, 6, 12, 18, 24 | T03 |

TABLE 12-continued

Summary of Stability Test Articles

| Test Article ID[1] | True Name[2] | Manufacturer | Storage Temp | Volume/ Vial (mL) | Number of Vials Prepared | Lot Number | Stability Testing Dates (month) | 6 Month Trt Group |
|---|---|---|---|---|---|---|---|---|
| BSA/Adj06/cold | S-50 ug BSA + Adjuvant 06 | | 2-7° C. | 5 | 26 | VACO2376-BSA/Adj06/cold-21 Nov. 2013 | 0, 6, 12, 18, 24 | T06 |
| BSA/Adj06/RT | S-50 ug BSA + Adjuvant 06 | | 18-27° C. | 5 | 26 | VACO2376-BSA/Adj06/RT-21 Nov. 2013 | 0, 6, 12, 18, 24 | T07 |

[1]Remaining volume from each aliquot used to inoculate on days 0 and 14 will be destroyed on day of use. The remaining retention aliquot will be retained.

TABLE 13

Adjuvant Stock Identification

| Adjuvant Catalog Number[1] | Manuf | Lot Number | Expiration Date | LTS Reference[2] | Adjuvant Label Information[3] | Storage |
|---|---|---|---|---|---|---|
| 70X0106 | BBL | 00003 | 7 Oct. 2015 | LTS-006-00 | Finished Vials Catalog No. 70X0106; Lot No. 00003 Store at 2-7° C./Do not Freeze; NOT FOR USE IN HUMANS; SAMPLE. For Research Only Expiration Date: 7 Oct. 2015 | −7° C. or 18-27° C. in same location as stability samples |

[3] Each adjuvant 5.0X stock was tested for purity and pH. All of the test articles will be handled aseptically during preparation; final test articles will not undergo further testing.

TABLE 14

Stability Test Article Descriptions

| Trt Grp | True Name[1] | Descriptor[2] | Storage Temperature[3] |
|---|---|---|---|
| T01 | S-Placebo (PBS only) | S-PBS/cold | 2-7° C. |
| T02 | S-50 ug BSA + PBS | S-BSA/cold | 2-7° C. |
| T03 | S-50 ug BSA + PBS | S-BSA/RT | 18-27° C. |
| T06 | S-50 ug BSA + Adjuvant 06 | S-BSA + 06/cold | 2-7° C. |
| T07 | S-50 ug BSA + Adjuvant 06 | S-BSA + 06/RT | 18-27° C. |

[1]500 ug/ml BSA stock, 50 ug BSA/dose
[2]Descriptor for each treatment group

TABLE 15

Fresh Test Article Descriptions

| Trt Grp | True Name[1] | Descriptor[2] | Storage Temperature[3] | | |
|---|---|---|---|---|---|
| | | | BSA | PBS | Adjuvant |
| T08 | F-50 ug BSA + PBS | F-BSA | | | |
| T11 | F-50 ug BSA + Adjuvant 06 | F-BSA + 06/cold | | | 2-7° C. |
| T12 | F-50 ug BSA + Adjuvant 06 | F-BSA + 06/RT | | | 18-27° C.[5] |

[1]500 ug/ml BSA stock, 50 ug BSA/dose
[2]Descriptor for each treatment group
[3]Storage temperature of components used to prepare fresh test articles
[5]5x Adjuvant stocks stored in the same storage location and temperature as the stability samples stored at 18-27° C.

TABLE 16

Clinical Study Design

| Trt Grp[1] | Descriptor | Route[2] | No. Mice | Dose (mL) | Inoculation (Day) | Blood Collection (Day)[4] |
|---|---|---|---|---|---|---|
| T01 | S-PBS/cold | SC | 5 | 0.1 | 0, 14 | 13, 28 |
| T02 | S-BSA/cold | SC | 10 | 0.1 | 0, 14 | |
| T03 | S-BSA/RT | SC | 10 | 0.1 | 0, 14 | |
| T06 | S-BSA + 06/cold | SC | 10 | 0.1 | 0, 14 | |
| T07 | S-BSA + 06/RT | SC | 10 | 0.1 | 0, 14 | |
| T08 | F-BSA | SC | 10 | 0.1 | 0, 14 | |
| T11 | F-BSA + 06/cold | SC | 10 | 0.1 | 0, 14 | |

TABLE 16-continued

Clinical Study Design

| Trt Grp [1] | Descriptor | Route [2] | No. Mice | Dose (mL) | Inoculation (Day) | Blood Collection (Day)[4] |
|---|---|---|---|---|---|---|
| 112 | F-BSA + 06/RT | SC | 10 | 0.1 | 0, 14 | |
| Additional [3] | Baseline | N/A | 20 | N/A | N/A | ** |

[1] For this study, the treatment group (TG) designation will identify the mice and the test article
[2] Mice will be inoculated via subcutaneous injection dorsal, between the shoulders
[3] Additional mice NOT inoculated with test article; used to obtain baseline blood samples
[4] 18-month study was ended on day 14

TABLE 17

Study Design

| Day | Activity |
|---|---|
| Days −6 to −8 | Daily Clinical Observations |
| Day −4-0 | Blood collection (baseline mice only) mice bled one time within this period to obtain prescreen samples for confirmation of mice |
| Day 0 | Treatment Administration |
| Day 1-28 | Blood collection (baseline mice only) mice bled periodically during this time to obtain baseline blood samples Daily Clinical Observations |
| Day 13 | Blood collection |
| Day 14 | Treatment Administration |
| Day 28 | Blood collection |

*18-mont study was ended on day 14 with no booster administration

Treatment Administration—Day 0

Mice were examined for normal health and appearance and enrolled in the study. Each cage represented a treatment group.

One vial of each treatment group preparation was aseptically divided into three aliquots. One aliquot was administered to the mice immediately (Day 0). One aliquot was stored at 2-7° C. until administered to the mice on Day 14. The last aliquot was maintained at 2-7° C. as a retention sample. All treatment group preparations (for each TG) were administered to mice subcutaneously dorsal between the shoulders according to the Study Design.

Sample Collection—Day 1-28 (Baseline Mice Only)

Blood was collected and pooled from the baseline mice (the mice not used in the study) as needed between days 1 and 28. No more than 10% of the total blood volume based on the average weight of the mice were collected within a 3-4 week period. Blood was allowed to clot and then centrifuged to collect serum. The serum was then pooled and stored at 2-7° C. or −18±5° C. until used as a negative control in the ELISA.

Sample Collection and Testing

Blood was collected from each inoculated animal on days 13 and 28. No more than 10% of the total blood volume based on the average weight of the mice was collected within a 3-4 week period. Blood was allowed to clot and then centrifuged to collect serum. The serum was then stored at 2-7° C. or −18±5° C. until tested. Serum was then assayed for the level of seroconversion via ELISA.

Treatment Administration—Day 14

All treatment group preparations (for each TG) were administered to mice via subcutaneous injection, dorsal between the shoulders according to the Study Design.

Health Observations and Adverse Events

Clinical observations were recorded daily following test article administration, as indicated in the study timeline.

It is possible that mice will demonstrate some adverse reactions during the study, such as injection site reactions, which may include the following: abscess (collection of puss built-up within the tissue of the body), swelling <1.5-1.5 cm diameter, alopecia (hair loss), erythema (excessive site redness), granuloma (hard nodule palpatable), bleeding or ulcer (sore on skin). Observation of any adverse reaction were documented.

Assessment of Analysis/Data Analysis

Serum samples were assayed for serconversion via ELISA using BBL SOP AN-084. The level of antibody production in each serum sample for each treatment group was determined. Antibody production in the mice administered Adjuvant+BSA was compared to the antibody production in mice administered the BSA positive control. Antibody production in mice administered the various adjuvant formulations was compared. Antibody production in the mice administered test articles that had been stored for stability analysis was compared to the mice administered test articles prepared fresh on day 0 of this study.

Antibody production levels in mice inoculated in this study were compared to the antibody levels produced in the first stability study conducted.

Descriptive statistics will be used when appropriate to determine effectiveness of all treatment groups compared to the negative control. Geometric means and statistical significance will be determined by performing two-tailed Student's t-test or other appropriate method.

Results and Conclusions

TABLE 18

In vivo Stability Study through 6 months

| Treatment Group Descriptions - In vivo Stability Study | | | | | | | | Blood | |
|---|---|---|---|---|---|---|---|---|---|
| Trt Group | Description | Stability Sample?[1] | Storage Temp | Route [1] | No. of Mice | Dose (mL) | Day | Collections Day | |
| T01 | Placebo (PBS only) | Yes | 2-7° C. | SC | 5 | 0.1 | 0, 14 | 13 28 ± 2* | |
| T02 | 50 ug BSA + PBS | Yes | 2-7° C. | SC | 10 | 0.1 | 0, 14 | | |

TABLE 18-continued

In vivo Stability Study through 6 months

| Treatment Group Descriptions - In vivo Stability Study | | | | | | | Blood |
|---|---|---|---|---|---|---|---|
| Trt Group | Description | Stability Sample?[1] | Storage Temp | Route[1] | No. of Mice | Dose (mL) | Day | Collections Day |
| T03 | 50 ug BSA + PBS | Yes | 18-27° C. | SC | 10 | 0.1 | 0, 14 |
| T06 | 50 ug BSA + 70X0106 | Yes | 2-7° C. | SC | 10 | 0.1 | 0, 14 |
| T07 | 50 ug BSA + 70X0106 | Yes | 18-27° C. | SC | 10 | 0.1 | 0, 14 |
| T08 | 50 ug BSA + PBS | No | N/A | SC | 10 | 0.1 | 0, 14 |
| T11 | 50 ug BSA + 70X0106 | No | N/A | SC | 10 | 0.1 | 0, 14 |
| T12 | 50 ug BSA + 70X0106 | No | N/A | SC | 10 | 0.1 | 0, 14 |

*Blood collection not completed yet (scheduled for 24 Jul. 2014)
**13,000 or 18,000 psi used in microfluidizer when preparing adjuvant
[1] 'Yes' = sample on stability; 'No' = Fresh sample prepared on day 0 of 6 month time point

TABLE 19

Mouse Stability GMT Values derived from ELISA Results
BSA + ENABL 06 on Stability through 6 months

| | | Time 0 | | | 6 Month | | |
|---|---|---|---|---|---|---|---|
| | | Day 32 | | | Day 28/29 | | |
| Treatment Group | Descriptor | Geometric Mean[1] | Incidence | Normalized* | Geometric Mean[1] | Incidence | Normalized* |
| T01 | S-PBS/2-7° C. | 10 | 0/4 | | 20 | 0/5 | |
| T02 | S-BSA/2-7° C. | 290 | 8/10 | 1 | 149 | 8/10 | 1 |
| T03 | S-BSA/RT | | | | 243 | 8/10 | 1 |
| T06 | S-BSA + 06/2-7° C. | 27,160 | 10/10 | 93.7 | 28,522 | 10/10 | 191.4 |
| T07 | S-BSA + 06/RT | | | | 30,177 | 10/10 | 124.2 |
| T08 | F-BSA | | | | 98 | 6/10 | |
| T11 | F-BSA + 06/2-7° C. | | | | 17,743 | 10/10 | 119.1 |
| T12 | F-BSA + 06/RT | | | | 34,297 | 10/10 | 141.1 |

TABLE 20

Mouse Stability GMT Values derived from ELISA Results
BSA + Adjuvant 06 on Stability Through 18 Months

| | | Time 0 | | | 18 Month | | |
|---|---|---|---|---|---|---|---|
| | | Day 13 | | | Day 14 | | |
| Treatment Group | Descriptor | Geometric Mean[1] | Incidence | Normalized* | Geometric Mean[1] | Incidence | Normalized* |
| T01 | S-PBS/2-7° C. | 10 | 0/4 | | 10 | 0/5 | |
| T02 | S-BSA/2-7° C. | 26 | 4/8 | 1 | 80 | 9/10 | 1 |
| T03 | S-BSA/RT | | | | 61 | 8/10 | 1 |
| T06 | S-BSA + 06/2-7° C. | 4,255 | 8/8 | 163.7 | 5,278 | 10/10 | 66.0 |
| T07 | S-BSA + 06/RT | | | | 12,996 | 10/10 | 213.0 |
| T08 | F-BSA | | | | 98 | 9/10 | 1 |
| T11 | F-BSA + 06/2-7° C. | | | | 6,063 | 10/10 | 61.9 |
| T12 | F-BSA + 06/RT | | | | 5,657 | 10/10 | 57.7 |

*Normalized to the respective BSA only GMT value

TABLE 21

Data from blood collected

| Descriptor | Incidence[1] | Geometric Mean[2] | Normalization[3] |
|---|---|---|---|
| PBO | 0/5 | 10 | ND[4] |
| BSA/PBS | 8/10 | 290 | 93.7 |
| BSA/Adj06 | 10/10 | 27,160 | |

[1] # Mice Seroconverted/# Mice Treated
[2] A value of 10 used for no seroconversion
[3] Geomean BSA/Adj06 ÷ Geomean BSA/PBS
[4] Not done

TABLE 22

Data at Time Point = 6 Months

| Descriptor | Incidence[1] | Geometric Mean[2] | Normalization[3] |
|---|---|---|---|
| S-PBO | 0/5 | 10 | Not determined |
| S-BSA/PBS/cold | 8/10 | 149 | 191.4 |
| S-BSA/Adj06/cold | 10/10 | 28,522 | |
| S-BSA/PBS/RT | 8/10 | 243 | 124.2 |
| S-BSA/Adj06/RT | 10/10 | 30,177 | |
| F-BSA/PBS | 6/10 | 98 | |
| F-BSA/Adj06/cold | 10/10 | 17,743 | 181.1 |
| F-BSA/Adj06/RT | 10/10 | 34,297 | 350.0 |

[1] #Mice Seroconverted/# Mice Treated
[2] A value of 10 used for no seroconversion
[3] Geomean BSA/Adj06 ÷ Geomean BSA/PBS

TABLE 23

Data at Time Point = 18 months

| Descriptor | Incidence[1] | Geometric Mean[2] | Normalization[3] |
|---|---|---|---|
| S-PBO | 0/5 | 10 | Not determined |
| S-BSA/PBS/cold | 9/10 | 80 | 66.0 |
| S-BSA/Adj06/cold | 10/10 | 5,278 | |
| S-BSA/PBS/RT | 8/10 | 61 | 213.0 |
| S-BSA/Adj06/RT | 10/10 | 12,996 | |
| F-BSA/PBS | 6/10 | 98 | Not determined |
| F-BSA/Adj06/cold | 10/10 | 6,063 | 61.9 |
| F-BSA/Adj06/RT | 10/10 | 5,657 | 57.7 |

[1] # Mice Seroconverted/# Mice Treated
[2] A value of 10 used for no seroconversion
[3] Geomean BSA/Adj06 ÷ Geomean BSA/PBS

TABLE 24

Geometric Means at 6 months

| | Geometric Means | | | |
|---|---|---|---|---|
| | | | Time point - 6 Months | |
| Descriptor | Time point - 0 Month | Fresh | Stability Cold - Storage (2-7° C.) | Stability Ambient - Storage (18-27° C.) |
| BSA/PBS | 290 | 98 | 149 | 243 |
| BSA/Adj06 | 27,160 | Fresh - Cold 17,743 | Fresh- Ambient 34,297 | 28,522 | 30,177 |
| Normalized BSA/Adj06 | 97.3 | Fresh - Cold 181.1 | Fresh- Ambient 350.0 | 191.4 | 124.2 |

TABLE 25

Geometric Means = 18 months

| | Geometric Means | | | |
|---|---|---|---|---|
| | | | Time point - 18 Months | |
| Descriptor | Time point - 0 Month (D14) | Fresh | Stability Cold - Storage (2-7° C.) | Stability Ambient - Storage (18-27° C.) |
| BSA/PBS | 26 | 98 | 80 | 61 |
| BSA/Adj06 | 4,255 | Fresh - Cold 6,063 | Fresh- Ambient 5,657 | 5,278 | 12,996 |
| Normalized BSA/Adj06 | 163.7 | Fresh - Cold 61.9 | Fresh- Ambient 57.7 | 66.0 | 213.0 |

The data shows that the adjuvants of the present invention were stable over an 18 month period. As can be seen from the data, all of the samples of adjuvant 06 were stable after 18 months. This data shows that the adjuvants of the present invention have shelf stability at ambient temperatures for at least 18 months. This allows for the ease of shipping, storage, and the use of the adjuvant either un-assembled or assembled with antigen.

Example 5

Material and Methods

Seventy one day old layer chicks were vaccinated with either 0.2 ml of the DNA vaccine given subcutaneously or with 0.2 ml of PBS. The DNA vaccine was a eukaryotic DNA vaccine plasmid backbone containing the HA gene from GyrFalcon/Washington/41088-6/2014. A total of 60 chicks were administered the DNA vaccine and 10 chicks were used as controls. At 2 weeks after the original vaccination, 20 chicks were boostered with 0.2 ml of DNA vaccine, and 20 chicks were vaccinated with 0.2 ml of the GyrFalcon/Washington/41088-6/2014 reverse genetics killed vaccine given with an adjuvant. Challenge was conducted when the birds were 4 weeks of age (2 to 4 weeks a weeks after the last vaccination) with A/Turkey/Minnesota/12582/2015 (H5N2) at a dose of $10^{6.5}$/EID50 administered in a dose of 0.5 ml by the choanal route of inoculation. The challenge virus was from a recent outbreak and the challenge dose was designed to give 1000 chicken lethal dose$_{50}$ as a stringent challenge.

Determination of viral shedding. Oropharyngeal swab samples from chickens were suspended in 2 ml sterile brain heart infusion (BHI) broth (Sigma-Aldrich, St. Louis, Mo.) containing 1× antibiotic/antimycotic (Mediatech, Herndon, Va.), and frozen at −70° C. until RNA extraction. Total viral RNA from 250 ul of sample was added to Trizol and after the addition of chloroform the aqueous phase was used with the MagMAX-96 AI/ND Viral RNA Isolation Kit (Ambion, Inc., Austin, Tex.). The procedure for RNA isolation was carried out using the KingFisher magnetic particle processing system (Thermo Scientific, Waltham, Mass.).

Quantitative real-time RT-PCR (RRT-PCR) was performed using primers and probe specific for type A avian influenza matrix gene (2). The AgPath-ID RT-PCR Kit (Invitrogen, Carlsbad, Calif.) was used with eight μl of the RNA sample and nuclease-free water were added to make a final volume of 25 μl. The reverse transcription reaction consisted of one cycle of 30 min. at 50° C., followed by 15 min. at 95° C. Forty cycles of 1 s denaturation at 94° C., followed by annealing for 20 s at 60° C. were carried out in the PCR reaction. Both reactions were carried out in a Smart Cycler II (Cepheid, Sunnyvale, Calif.) real-time PCR machine. The $EID_{50s}$ of virus from the swab samples were extrapolated from the cycle thresholds by using standard curves generated from the known amounts of RNA of the challenge viruses used (1). Detection limits of each RRT-PCR run were calculated based on the standard curve, by setting the cycle threshold values equal to the number of cycles run. For statistical purposes, samples that were RRT-PCR-negative in this study were assigned a cycle threshold value of 1 cycle below the lowest detection point in the standard curve.

A Hemagglutination inhibition (HI) test was then performed. Hemagglutination inhibition antibody titers against AIV were determined by using the HI test (3). Homologous beta-propiolactone-inactivated antigen (Ag) was diluted in PBS to make a concentration of four HA units. Homologous Ag refers to the A/gyrfalcon/Washington/41088-6/2014 H5N8 virus which is the same hemagglutinin gene as used in the RP vaccine except the RP gene was modified to have a low pathogenic cleavage site which does not affect the antigenicity of the virus. Fifty microliters of Ag were added per well of a 96-well plate, where test serum was two-fold, serially diluted. Plates were incubated for 15 min. at room temperature before 0.5% chicken red blood cells were added to each well. Plates were shaken for 15 s, and incubated for 45 min. at room temperature. Results were interpreted as the reciprocal of the last well that had complete inhibition of hemagglutinating activity. For statistical purposes a reciprocal titer of 4 was considered the lowest positive result.

Results and Conclusions

The vaccinated and control birds were challenged with A/Turkey/Minnesota/12582/2015 (H5N2) at 2 or 4 weeks after the last vaccination. All the control birds showed severe clinical disease or death by 3 days post-challenge with a Mean Death Time (MDT) of 2.1 days, and birds with severe clinical disease were euthanized and recorded as dead the following day as required under the IACUC protocols (FIG. 1).

Serology was conducted on blood taken at the day of challenge, 4 weeks of age and 2 or 4 weeks after vaccination. None of the control birds or the single DNA vaccinated birds had detectable HI antibody titers. Of the vaccinated birds, 7 of 20 birds had detectable antibody titers ranging from 4 to 32 in the twice DNA vaccinated group and 19 of 20 birds had titers in the DNA/RG group. The geometric mean titer for the birds that seroconverted were 8.8 ($2^{3.14}$) and 16.6 ($2^{4.05}$) respectively. (Table 26)

Viral shedding post-challenge. All the control birds died or were euthanized on day 3 post-challenge, but all birds, dead or alive, were oropharyngeally swabbed on day 2. All vaccinated birds were swabbed at day 2 and all remaining birds were sampled on day 4 post-challenge. The control birds on day 2 were shedding $10^{7.1}/EID_{50}$ with all birds shedding similar titers of virus. The single DNA vaccinated birds at day 2 were shedding $10^{6.6}/EID_{50}$, the double DNA vaccinated group were shedding $10^{5.4}/EID_{50}$ logs of virus, and the DNA/RG vaccinated group were shedding $10^{2.9}/EID50$ logs of virus respectively (FIG. 1). The amount of virus shedding was statistically different (P=<0.001) between the controls and twice DNA vaccinated group and the DNA/RG vaccinated birds on day 2 using the Mann-Whitney Rank Sum Test.

The prime boost vaccine approach of the DNA vaccine at a day of age and a booster at 2 weeks was 95% effective against challenge while the treatment group given the 2 dose DNA vaccine provided protection in 55% of the vaccinated birds. The correlation was extremely high that the birds that seroconverted on the HI test with at least a titer of 4 survived challenge and had reduced shedding. These results indicate that the DNA vaccine can be used in stand alone or combination vaccination trials.

TABLE 26

Hemagglutination Inhibition Titers by individual vaccinated bird.

|  | GMT |
|---|---|
| G1 Sham | 0 |
| G2 DNA vx/single | 0 |
| G3 DNA vx + DNA boost | 8.8 |
| G4 DNA vx + rgH5 boost 4 | 16.6 |

Hemagglutination Inhibition titers by individual vaccinated bird. The minimal positive HI titers was 4, so measured titers of 2 were converted to 0 for calculation. For geometric mean titers, the birds with negative titers were not included in the calculation.

Example 6

Efficacy Study for the Serological Assessment of DNA Vaccine Combined Adjuvant of the Present Disclosure in Turkeys The purpose of this study was to establish a reasonable expectation of efficacy for a High Pathology Avian Influenza (HPAI) DNA vaccine using the adjuvants of the present disclosure. This was accomplished by assessing the ability of the vaccine to elicit an immune response in turkeys. To this end, a plasmid DNA containing a modified gene for the high path avian influenza virus, A/gryfalcon/WA/41088-6/2014 H5N8, hemagglutinin (HA) protein was combined with VaxLiant adjuvants and administered via the subcutaneous and intranasal routes.

The modified plasmid, NTC8685-eRNA41H-KP307984.1-HA-Modified encodes the HA gene from highly pathogenic (HP) Avian Influenza Virus (AIV) strain A/gyrfalcon/Washington/41088-6/2014 (H5N8). The H5 sequence was modified to change the HP multibasic cleavage site (PLRERRRKRGLF) to a monobasic cleavage site. The modified H5 gene was produced synthetically, cloned into the NTC8685-eRNA41H optimized eukaryotic expression vector, and the construct was transformed into the into E. coli strain NTC4862.

Efficacy was measured by testing for seroconversion to the inactivated virus containing the unmodified HA gene using a hemagglutination inhibition assay.

Materials and Methods

ENABL 1 and 0.5×ENABL™ 5 with pHA DNA (IVP 1 and 2) or phosphate buffered saline (PBS) with pHA DNA (MPC), was administered subcutaneously (SC) in each bird. Each IVP treatment group included a minimum of 22 birds and the MPC group 10 birds, were inoculated on Day 0. Birds were observed for overall general health for the entire study. All birds were inoculated on study day 0. Blood was collected approximately 2 weeks after each inoculation and tested for seroconversion.

TABLE 27

Study Description

| TG | Description | Route [1] | No. of Birds | Vaccination (Day) | Blood Collection (Day) |
|---|---|---|---|---|---|
| T01 | PBS Control (MPC-1) | SC/base of neck | 10 | 0, 14 | 13, 28 (terminal) |
| T02 | pHA DNA + 0.5X ENABL 5 (IVP-1) | SC/base of neck | 22 | 0, 14 | 13, 28 (terminal) |
| T03 | pHA DNA + 0.5X ENABL 5 (IVP-1) | SC/base of neck | 22 | 0* | 21 |

[1] SC—subcutaneous at the base of the neck; IN—intranasal

TABLE 28

Test Articles

| ID | Lot | Description per Dose | Lot Testing |
|---|---|---|---|
| MPC-1 | TBD | Phosphate Buffered Saline | N/A - commercial |
| IVP-1 | HA-060715-30BM13 | 30 ug pHA-hp5 with 0.5X ENABL | Purity and Identity |

TABLE 29

Study Timeline

| Day | Activity |
|---|---|
| Day 0 | Day of Arrival |
|  | Test Article Administration |
| Day 13-14 | Blood Collection (T01, 02) |
|  | Test Article Booster Administration (T01, 02) |
| Day 21 | Blood Collection (T03) |
| Day 28 | Blood Collection (T01, 02, 03) |
| Days 0-28 | Daily Clinical Observations |
| Day 28 | End of Study, Bird reconciliation |

Administration Route. Birds were administered the test articles either by subcutaneous injection in the back of the neck, or intranasally dripped into the nares. The Test Article was administered at Days 0 and 14. The birds in T01 received PBS via the SC route and represent the MPC-1. The remaining birds were inoculated as described in the Study Design. On Day 14, birds in groups T01, 02 received product and this was the boost. Birds in groups T03 did not receive a boost.

Sample Collection and Testing. Blood was collected from each bird in groups T01, 02 prior to the day of booster administration of test articles and at the end of the study according to site procedures. Birds in groups T03 were bled on day 21 and at the end of the study. Blood was allowed to clot and then centrifuged to collect serum. The serum was stored at 2-7 or −18±5° C. Serum was assayed for the level of seroconversion via inhibition of 4-8 hemagglutination units of the virus, A/gyrfalcon/WA/41088-6/2014 H5N8 BEI per BBL SOP LP-054.

Assessment of Results/Data Analysis. Serum was assayed for the level of seroconversion via inhibition of hemagglutination of the virus, A/gyrfalcon/WA/41088-6/2014 H5N8 BEI inact, which contained the unmodified HA gene, per BBL SOP LP-054. The hemagglutination inhibition (HAI) titer was determined for each serum sample in each treatment group. Briefly, serial dilutions of the serum were incubated with 4-8 hemagglutinin units and finally added to chicken red blood cells. The HAI titer was reported as the inverse log of the last dilution where there is 100% inhibition of viral-specific hemagglutination in all replicates. The HAI titers in the birds administered the various adjuvant formulations were compared.

TABLE 30

Results. Turkey Efficacy

| Turkey Efficacy, Day of hatch vaccination | | # birds | Vaccinations | Blood Collection (day) | GMT HAI of seroconverted birds |
|---|---|---|---|---|---|
| T01 | PBS | SQ | 10 | primary (Day 0) | 14, 28 | 2 |
| T02 | 30 ug/0.2 mL, LP7, HPAI HA-mod (fresh) | SQ | 22 | primary (0), boost (14) | 14, 28 | 10.6 |
| T03 | 30 ug/0.2 mL, LP7, HPAI HA-mod (fresh) | SQ | 22 | primary (Day 0) | 21 | 2 |

Results indicate that turkeys can be vaccinated with the HPAI DNA/adjuvant combination at one day of age. Furthermore, that birds seroconverting would be protected against homologous challenge with two dose regimen when administered SC with the formulation tested in this study.

Example 7

The adjuvant formulas of the present disclosure to be tested as the investigational veterinary products (IVPs) in this turkey study were ENABL® 1 and 6 formulated with a plasmid DNA (pHA) containing a modified hemagglutinin (HA) gene from a highly pathogenic (HP) Avian Influenza Virus (AIV) strain A/gyrfalcon/Washington/41088-6/2014 (H5N8). The H5 sequence was modified to change the HP multibasic cleavage site (PLRERRRKRGLF) (SEQ ID NO. 1) to a monobasic cleavage site. The modified H5 gene was produced synthetically, cloned into the NTC8685-eRNA41H optimized eukaryotic expression vector. The same pHA was mixed with phosphate buffered saline (PBS) to serve as the study's matched placebo control (MPC).

The purpose of this study was to establish a DNA vaccine withdrawal time of 21-days for turkeys inoculated with ENABL® 1 and ENABL® 6.

Materials and Methods
Study Design
ENABL 1 and ENABL™ 6 with pHA DNA (IVP 1 and 2) or phosphate buffered saline (PBS) with pHA DNA (MPC), was administered subcutaneously (SC) in each bird. Each treatment group consisted of a minimum of 10 birds inoculated on Day 0. Birds were observed for overall general health for twenty-one days. Site-specific observations were conducted on days 1 through 7, 14, and 21. All birds that were euthanized due to morbidity or found dead after Study Day 0 and before Day 21 were necropsied to determine if the death was a result of the IVP or MPC. All remaining birds on Day 21 had gross pathology and histological examinations. The study design is summarized in Table 31.

TABLE 31

Study Description

| Treatment Group | Product* | Number of Birds | Necropsy and Sample Day |
|---|---|---|---|
| T01 | pHA DNA + ENABL™ 1 (IVP- | 15 | 21 |
| T02 | pHA DNA + ENABL™ 6 (IVP- | 15 | 21 |
| T03 | pHA DNA + PBS (MPC) | 15 | 21 |

*Each product will be identified by the lot number assigned. A dose of 0.2 mL of the final products will be administered subcutaneously in the neck.

The test articles are described below. Prior to use in the study they were designated test article A through C, and identified as such during the study to maintain proper blinding.

TABLE 32 pHA DNA, containing ENABL® 1
(The Investigational Veterinary Product #1)

| | |
|---|---|
| True Name | Avian Influenza Vaccine, DNA, H5 Subtype |
| Formulation | 40% bulk pHA, 40% PBS and 20% ENABL® 1 |
| Storage Conditions | 2 to 7° C. |
| Treatment Route | SC - Neck |
| Testing Requirements | Plasmid DNA identity Satisfactory for purity |
| Product Preparation | IVP-1 will be supplied ready to use |
| Applied Dose | 1 dose-0.2 mL |

TABLE 33 pHA DNA, containing ENABL® 6
(The Investigational Veterinary Product #2)

| | |
|---|---|
| True Name | Avian Influenza Vaccine, DNA, H5 Subtype |
| Formulation | 40% bulk pHA, 40% PBS and 20% ENABL® 6 |
| Storage Conditions | 2 to 7° C. |
| Treatment Route | SC - Neck |
| Testing Requirements | Plasmid DNA identity Satisfactory for purity |
| Product Preparation | IVP-2 will be supplied ready to use |
| Applied Dose | 1 dose-0.2 mL |

TABLE 34 pHA DNA + PBS
(The Matched Placebo Control)

| | |
|---|---|
| True Name | Avian Influenza Vaccine, DNA, H5 Subtype |
| Formulation | 40% pHA DNA 60% PBS |
| Storage Conditions | 2 to 7° C. |
| Treatment Route | SC - Neck |
| Testing Requirements | Plasmid DNA identity Satisfactory for purity |
| Product Preparation | MPC will be supplied ready to use |
| Applied Dose | 1 dose-0.2 mL |

TABLE 35

Study Timeline

| Study Day | Activity |
|---|---|
| Day 0 | Tag |
| | Bird Health and Injection Site Evaluation |
| | Product Administration |
| Days 1-21 | General Clinical Observations |
| Days 1-7 | Injection Site Observation |
| Day 14 | Injection Site Observation |
| Day 21 | Injection Site Observation |
| | Necropsy and Sample Collection |

Treatment Administration—Day 0

Health assessment, clinical observations, and proposed injection site observations were recorded the day of treatment. Each bird was injected once in the subcutaneous space in the mid part of the back of the neck with the designated product. Dose was 0.2 mL per site.

Clinical Observations, Injection Site Observations, and Adverse Events

All the birds were observed daily for overall health status following test article administration, as indicated in the study timeline. Clinical signs were categorized according to standardized low-level terms developed by the Veterinary Dictionary for Drug Regulatory Activities (VEDDRA).

Injection sites were palpated, observed and recorded on Days 1-7, and day 14. On day 21 a final injection site palpation and exam occurred of all injected sites just prior to euthanasia and necropsy.

Sample Collection

For histological data collection, tissue samples were harvested from the injection sites and surrounding tissue. The pathologist examined the injection site for gross lesions related to injection site abnormalities.

Injection Site Examination and Scoring

The injection site was palpated and findings recorded. The skin was incised and the underlying tissue examined. A score for the injection site was assigned during necropsy by the pathologist, based on presence of any drainage tract, abscessation, edema, hemorrhage, or necrosis. The most severe manifestation at any given injection site determined the single injection site score assigned by the pathologist to the injection site. In the event more than one manifestation is observed at a single injection site, the other (lower and non-score-determining) manifestations were recorded, but these less severe findings did not reduce the score assigned based on the most severe manifestation.

Injection Site Histological Scoring

Each tissue collected was examined for histological evidence of site reactions. As for the gross necropsy findings, the MOST SEVERE grade was assigned to the injection site and used as the histology score for the site.

Results and Conclusions

For each treatment group 14 birds survived the initial placement and study period that met the criteria inclusion in the study due to health status at the time of acclimation. The results of the site observations and gross/histopathology at necropsy are provided in the following table.

TABLE 36

Results of Observations and Gross/Histopathology

| Treatment Group | Site Observations[1] | Gross Pathology at Injection site[2] | Histological (microscopic) examination at injection site[3] |
|---|---|---|---|
| Placebo control | 0 | 0 | 0 |
| T01 (pHA DNA + ENABL ™ 1 (IVP-1)) | 3/14 | 6/14 | 7/14 |
| T02 (pHA DNA + ENABL ™ 6 (IVP-2)) | 3/14 | 7/14 | 3/14 |

[1]Number of animals with visible swelling by end of the 21 day observation period
[2]Number of animals with noticeable inflammatory response at necropsy, mild to moderate.
[3]Number of animals with physiological response only observable microscopically at necropsy Site observations. None of the placebo inoculated birds were scored for any abnormal responses either at the site observation or necropsy level all birds scored negative for any type of clinical manifestations for vaccine or injury related pathology. For treatment group T01 and T02 only 3 of 14 birds (6 birds total) demonstrated some swelling at the site of inoculation that could be palpated at the end of the 21 day period. The remaining birds (22 birds) were normal.

Necropsy. At necropsy the overall gross pathology observations for T01 group indicated that 6 of 14 birds had no type of lesion or pathology associated with injection site at 21 days, of the 8 remaining birds only two birds had more severe inflammatory response, the remaining were moderate to mild. The overall histological results indicated that 7 of 14 birds had no visible infiltration indicative of inflammation or immune response at 21 days. Of the remaining 7 birds, the observations were moderate. None of the birds had visible bruising or hemorrhage related injury at the site of injection.

The overall gross pathology observations for the T03 treatment group, 7 of 14 birds had no type of lesion or pathology associated with injection site at 21 days, the 7 birds remaining there were mostly mild responses. The overall histological results indicated that 3 of 14 birds had no visible infiltration indicative of inflammation or immune response at 21 days, while the remaining 11 birds indicated some mild to moderate infiltration indicative of immune response or inflammation.

The adjuvants tested here showed very little site reactions visible during the 21 day observation, the animals remained healthy and were not in any discomfort. Only on necropsy could any pathology be seen by trained pathologist, that were also evident in histology sections my microscopic examination. None of the reactions observed at 21 days (end of study) at necropsy by gross pathology would have been considered severe enough to disrupt slaughter line for poultry processing. All lesions that could be scored upon necropsy were mild to moderate and appeared to be resolving themselves indicating that within time (several days) the tissue would return to normal appearance. These results indicate that the adjuvant would be considered for 21 day withdrawal safety approval, which is the lowest time allowed by USDA for use of an adjuvant with a vaccine formulation.

What is claimed is:

1. A vaccine composition comprising:
   an adjuvant composition comprising a lipophile and a polymer of acrylic or methacrylic acid; and
   an antigen selected from a human antigen, an equine antigen, a bovine antigen, a canine antigen, a feline antigen, a simian antigen, a caprine antigen, a porcine antigen, an avian antigen, or any combination thereof.

2. The vaccine composition of claim 1, wherein the adjuvant composition further comprises at least one component selected from the group consisting of saline, cholesterol, alcohol, a saponin, sodium hydroxide, immunomodulators, small molecules, cytokines, and any combination thereof.

3. The vaccine composition of claim 1, wherein the lipophile has medium chain triglycerides.

4. The vaccine composition of claim 1, wherein the polymer of acrylic or methacrylic acid is a carbomer.

5. The vaccine composition of claim 2, wherein the cholesterol is vegetable-derived cholesterol.

6. The vaccine composition of claim 2, wherein the alcohol is ethanol.

7. The vaccine composition of claim 2, wherein the saponin is Quil-A.

8. The vaccine composition of claim 1, wherein the vaccine composition is formulated for an administration route selected from the group consisting of needleless, transdermal, intravenous, intraperitoneal, intramuscular, and subcutaneous.

9. The vaccine composition of claim 1, wherein the antigen is selected from the group consisting of a nucleic acid, a virus, bacteria, and any combination thereof.

10. A method of vaccinating an animal comprising the steps of administering the vaccine composition of claim 1 to an animal in need thereof.

11. The method of claim 10, further comprising the step of formulating the vaccine composition for needleless administration.

12. The vaccine composition of claim 1, wherein the vaccine is effective when administered via an administration route selected from the group consisting of needleless, transdermal, intravenous, intraperitoneal, intramuscular, and subcutaneous.

13. The vaccine composition of claim 1, wherein the vaccine is effective when administered via a needleless route of administration.

14. The vaccine composition of claim 1, wherein the antigen is selected from the group consisting of *Mycoplasma hyopneumoniae*, avian influenza virus (AIV), swine influenza virus (SIV), porcine reproductive and respiratory syndrome (PRRS) virus, *Lawsonia intracellularis*, bovine viral diarrhoea virus (BVD), Border's disease virus, *Leptospira* spp., *Brucella* spp., *Clostridium* spp., *Salmonella* spp, *Escherichia coli*, swine pox virus, Eperythrozoonosis, classical swine fever (CSF), African swine fever (ASF), Pneumonic pasteurellosis, *Streptococcus* spp., *Pasteurella multocida*, *Streptococcus suis*, Streptococcal meningitis, rabies virus spp., pseudorabies, swine influenza virus, *Brachyspira pilosicoli, Brachyspira hyodysentheriae*, coronavirus, porcine parvovirus, *Actinobacillus pleuropneumonia, Haemophilus parasuis, Staphylococcus hyicus, Erysipelothrix rhusiopathia, Eperythrozoonosis suis*, encephalomyocarditis virus, herpes virus, bovine herpesvirus-1(BHV-1), porcine cytomegalovirus (PCMV), Japanese B encephalitis virus (JE), porcine epidemic diarrhoea virus (PED), porcine respiratory corona virus (PRCV), rotavirus spp., swine vesicular disease (SVD), *Mycobacterium tuberculosis*, virus of vesicular exanthema of swine (VES), vesicular stomatitis (VS) virus, and eastern equine encephalomyelitis viruses (EEEV).

15. The vaccine composition of claim 1, wherein the antigen is an avian antigen selected from DNA encoding the H5 gene of the avian influenza virus, and DNA encoding the HA gene of the Avian influenza virus strain A/gyrfalcon/Washington/41088-6/2014 (H5N8).

16. The vaccine composition of claim 1, wherein the antigen is capable of transdermal administration in combination with an adjuvant lacking lecithin.

17. The vaccine composition of claim 16, wherein the antigen is selected from the group consisting of *Mycoplasma hyorhinis, Mycoplasma bovis, Fusobacter nephacorum, Klebsiella* spp., Porcine Circovirus (PCV), *Actinobaccilus suis, Anaplasma phagocytophilum*, Mannheimia Haemolytica, Pasteurella Multocida, BVD Type 1, BVD Type 2, parainfluenza 3 virus, bovine respiratory syncytial virus (BRSV), foot and mouth disease (FMD) virus, Rift Valley fever (RFV) virus, Pseudorabies Virus, Nipah Virus, Influenza A, Ebola virus, Reston virus, teschovirus spp., Japanese encephalitis virus, Getah virus, transmissible gastroenteritis virus (TGE), Menangle Virus, vesicular exanthema of swine virus, porcine rubulavirus, Seneca Valley virus, porcine deltacoronavirus, porcine parainfluenza 1 virus, atypical swine pestivirus, influenza C virus, hemagglutinating encephalomyelitis virus, hepatitis E virus, porcine adenovirus, porcine kobuvirus, porcine sapovirus, *orthoreovirus* spp., Sendai virus, Chikungunya virus, porcine bocavirus, porcine astrovirus, porcine sapelovirus, porcine torovirus, swine papillomavirus.

* * * * *